US008303964B2

(12) United States Patent
Woodard et al.

(10) Patent No.: US 8,303,964 B2
(45) Date of Patent: Nov. 6, 2012

(54) VIABLE NON-TOXIC GRAM-NEGATIVE BACTERIA

(75) Inventors: Ronald Wesley Woodard, Ann Arbor, MI (US); Timothy Charles Meredith, Ann Arbor, MI (US); Parag Aggarwal, Frederick, MD (US)

(73) Assignee: Research Corporation Technologies, Inc., Tucson, AZ (US)

( * ) Notice: Subject to any disclaimer, the term of this patent is extended or adjusted under 35 U.S.C. 154(b) by 1262 days.

(21) Appl. No.: 11/655,413

(22) Filed: Jan. 19, 2007

(65) Prior Publication Data
US 2010/0272758 A1 Oct. 28, 2010

Related U.S. Application Data

(60) Provisional application No. 60/760,314, filed on Jan. 19, 2006.

(51) Int. Cl.
*A61K 39/095* (2006.01)
(52) U.S. Cl. .................................... 424/249.1
(58) Field of Classification Search .......................... None
See application file for complete search history.

(56) References Cited

U.S. PATENT DOCUMENTS

| 6,558,677 | B2 | 5/2003 | Zollinger |
| 7,011,836 | B1 | 3/2006 | Van der Ley |
| 7,384,645 | B2 | 6/2008 | Foster |
| 2005/0106184 | A1 | 5/2005 | Franks et al. |

FOREIGN PATENT DOCUMENTS

| WO | 98/53851 | 12/1998 |
| WO | 2005/064021 | 7/2005 |
| WO | 2005/064021 A2 | 7/2005 |

OTHER PUBLICATIONS

Tzeng, Y.L. et al., "Endotoxin of *Neisseria Meningitidis* Composed Only of Intact Lipid A: Inactivation of the Meningococcal 3-Deoxy-D-Manno-Octulosinic Acid Transferase" *Journal of Bacteriology* (2002) pp. 2379-2388, vol. 184(9).
European Office Action dated Mar. 22, 2010.
Supplementary European Search Report, EP Patent Application No. 07718326.7, mailed May 26, 2009.
Caroff, et al., "Structure of bacterial lipopolysaccharides," Carbohydrate Research, Elsevier Scientific Publishing Company, Amsterdam, NL, vol. 338, No. 23, Nov. 14, 2003.
Vorachek-Warren, et al., A triple mutant of *Escherichia coli* lacking secondary acyl chains on lipid A, Journal of Biological Chemistry, vol. 277, No. 16, Apr. 19, 2002.
Vuorio, R., et al., "The Lipid A Biosynthesis Mutation LPXA2 of *Escherichia-coli* Results in Drastic Antibiotic Supersusceptibility," Antimicrobial Agents and Chemotherapy, vol. 36, No. 4, 1992.
Belunis, C.J., et al. "Inhibition of Lipopolysaccharide Biosynthesis and Cell Growth following inactivation of the kdtA Gene in *Escherichia coli*," J. Biol. Chem. 270 27646 (1995).
Borgstrom, B, "Bile Salts—Their Physiological Functions in the Gastrointestinal Tract," Acta Med. Scand. 196, 1 (1974).
Brade, O., et al., "An Artificial Glycoconjugate Containing the Bisphosphorylated Glucosamine Disaccharide Backbone of Lipid A Binds Lipid A Monoclonal Antibodies" Infect. Immun. 61, 4514 (1993).
Brozek, K.A., C.R. Raetz, "Biosynthesis of Lipid A in *Escherichia coli*," J. Biol. Chem. 265, 15410 (1990).
Bulieris, P.V., et al., "Folding and Insertion of the Outer Membrane Protein OmpA is Assisted by the Chaperone Skp and by Lipopolysaccharide," J. Biol. Chem. 278, 9092 (2003).
Datsenko, B., L., "One-step Inactivation of Chromosomal Genes in *Escherichia coli* K-12 using PCR Products" Wanner, Proc. Natl. Acad. Sci, U.S.A. 97, 6640 (2000).
De Cock, H., et al., "Lipopolysaccharides and divalent cations are involved in the formation of an assembly-competent intermediate of outer-membrane protein PhoE of *E. coli*," Embo J. 15, 5567 (1996).
Doerrler, W.T., et al., "ATPase Activity of the MsbA Lipid Flippase of *Escherichia coli*," J. Biol. Chem. 277, 36697-36705 (2002).
Donnenberg, et al. 1994,"Internalization of *Escherichia coli* into Human Kidney Epithelial Cells: Comparison of Fecal and Pyelonephritis-Associated Strains," J. Infect. Dis. 169:831.
Evans, et al., 1975, "Plasmid-Controlled Colonization Factor Associated with Virulence in *Escherichia coli* Enterotoxigenic for Humans," Infect. Immun. 12:656.
Fujishima, H., "kdsA mutations affect FtsZ-ring formation in *Escherichia coli* K-12," Microbiology, Jan. 2002, vol. 148, No. 1, pp. 103-112.
Galloway, C.R. Raetz, "A Mutant of *Escherichia coli* Defective in the First Step of Endotoxin Biosynthesis," J. Biol. Chem. 265 6394 (1990).
Goldman, R.C., et al., "Molecular Cloning of the Structural Gene Coding for CTP:CMP-3-Deoxy-manno-Octulosonate Cytidylytransferase from *Escherichia coli* K-12" J. Bacteriol. 163, 256 (1985).
Golenbock, D.T., et al.,"Lipid A-like Molecules that Antagonize the Effects of Endotoxins on Human Monocytes," J. Biol. Chem. 266, 19490 (1991).
Grant, et al., 1990, "Differential Plasmid rescue from thrangenic Mouse DNAs into *Excherichia coli* methylation-restriction mutants" Proc. Natl. Acad. Sci, USA, 87:4645.
Gronow, et al., "Lipopolysaccharide biosynthesis: which steps do bacteria need to survive?" J. Endotoxin Res. 7, 3 (2001).
Hancock, et al., "Interaction of Amino glycosides with the Outer Membranes and Purified Lipopolysaccharide and OmpF Porin of *Escherichia coli*," Antimicrob. Agents. Chemother. 35, 1309 (1991).
Heine, H., et al., "The Biology of Endotoxin," Mol. Biotechnol. 19, 279 (2001).
Holst, O., "Chemical Structure of the Core Region of Lipopolysaccharides—an Update" Trends Glycosci. Glycotechnol. 14, 87 (2002).
Imoto, M., et al. "Chemical Synthesis of a Biosynthetic Precursor of Lipid A with a Phosphorylated Tetraacyl Disaccharide Structure" Bull. Chem. Soc. Japan 60, 2197 (1987).
International Search Report and Written Opinion dated Oct. 5, 2007, PCT/US07/01367.

(Continued)

*Primary Examiner* — Gary Nickol
*Assistant Examiner* — Khatol Shahnan-Shah
(74) *Attorney, Agent, or Firm* — Scully, Scott, Murphy & Presser, P.C.

(57) ABSTRACT

The present invention provides non-toxic Gram-negative bacteria. In particular, the present invention provides viable Gram-negative bacteria (e.g., *E. coli*) substantially lacking lipopolysaccharide (LPS, endotoxin) within the outer membrane. The present invention further provides methods of generating viable non-toxic Gram-negative bacteria and uses thereof. The present invention also provides compositions and methods for inducing immune responses and for researching and developing therapeutic agents.

16 Claims, 11 Drawing Sheets

OTHER PUBLICATIONS

Kuhn, H.M., et al., "ECA, the enterobacterial common antigen", FEMS Microbiol. Rev. 4, 195 (1988).

Leive, L., Ann. N.Y. The Barrier Function of the Gram-Negative Envelope, Acad. Sci, 235, 109(1974).

McKee and O'Brien, "Investigation of Enterohemorrhagic *Escherichia coli* O157:H7 Adherence Characteristics and Invasion Potential Reveals a New Attachment Pattern Shared by Intestinal *E. coli*," 1995, Infect. Immun. 63:2070.

Meredith, T.C. & Woodard, R.W. "*Escherichia coli* YrbH is a D-Arabinose 5-Phosphate Isomerase," (2003) J. Biol. Chem. 278, 32771-7.

Meredith et al., "Redefining the requisite lipopolysaccaride structure in *Escherichia coli*," ACS Chem. Biolog., Feb. 2006, vol. 17, No. 1, pp. 33-42.

Meredith & Woodard, "Identification of GutQ from *Escherichia coli* as a D-Arabinose 5-phosphate isomerase,"Journal of Bacteriology. Oct. 2005, vol. 187, No. 20, pp. 6936-6941.

Mueller, M., et al. "Aggregates Are the Biologically Active Units of Endotoxin" J. Biol. Chem. 279, 26307 (2004).

Muller-Loennies, S., et al. "Structural Analysis of Oligosaccharides from Lipopolysaccharide (LPS) of *Exeherichia coli* K12 Strain W3100 Reveals a Link Between Inner and Outer Core LPS Biosynthesis" J. Biol. Chem. 278, 34090 (2003).

Nikaido, H., "Molecular Basis of Bacterial Outer Membrane Permeability Revisited," Microbiol. Mol. Biol. Rev. 67, 593 (2003).

Pantophlet, et al., "Detection of lipid A by monoclonal antibodies in S-form lipopoly-saccharide after acidic treatment of immobilized LPS on Western blot," J. Endotoxin Res. 4, 89 (1997).

Polissi, A., and Georgopoulos, C. "Mutational analysis and properties of the msbA gene of *Escherichia coli*, coding for an essential ABC family transporter" Mol. Microbiol. 20, 1221-1233 (1998).

Raetz, C.R., Whitfield, "Lipopolysaccharide Endotoxins," I Annu. Rev. Biochem. 71, 635 (2002).

Rick, P.D., et al. "Isolation of a Mutant of *Salmonella typhimurium* Dependent on D-Arabinose-5-phosphate for Growth and Synthesis of 3-Deoxy-D-mannoctulosonate (Ketodeoxyoctonate)" Proc. Natl. Acad. Sci U.S.A. 69, 3756 (1972).

Sansonetti, et al., "Plasmid-Mediated Invasiveness of Shigella-Like *Escherichia coli*," 1982 Ann. Microbiol. (Inst. Pasteur), 132A:351).

Sen, K., et al., "Lipopolysaccharide Structure Required for in Vitro Trimerization of *Escherichia coli* OmpF Porin," J. Bacteriol. 173, 926 (1991).

Tan & Darby, "*Yersinia pestis* is viable with endotoxin composed of only lipid," A Journal of Bacteriologyo, Sep. 2005, vol. 187, No. 18, pp. 6599-6600.

Tzeng, et al., "KpsF is the Arabinose-5-phosphate isomerase required for 3-Deoxy-D-manno-octulosonic acid biosynthesis and for both lipoligosaccharide assembly and capsular polysaccharide expression in *Neisseria meningitides*.,"The Gournal of Biological Chemistry, Jul. 2002, vol. 277, No. 27, pp. 24103-24112.

Van Abmersfoort, et al., "Receptors, Mediators, and Mechanisms Involved in Bacterial Sepsis and Septic Shock,", Clin. Microbiol. Rev. 16, 379 (2003).

Van Der Ley, P., et al., "KLessons from an LPS-deficient *Neisseria meningitides* mutant," J. Endotoxin, Res. 9, 124 (2003).

Wiese et al., "Molecular Mechanisms of Polymyxin B-Membrane Interactions: Direct Correlation Between Surface Charge Density and Self-Promoted Transport," J. Membr. Biol. 162, 127 (1998).

Wiese, et al., "The Dual Role of Lipopolysaccharide as Effector and Target Molecule," Biol. Chem. 380, 767 (1999).

Yamada, M. et al. "Nucleotide sequence and expression of the gut! Gene within the glucitol operon of *Escherichia coli*," (1990) DNA Seq 1, 141-5.

Zhou, Z., et al., "Function of *Escherichia coli* MsbA, an Essential ABC Family Transporter, in Lipid A and Phospholipid Biosynthesis," J. Biol. Chem. 273, 1246-12475 (1998).

Raetz, C. et al., "Lipopolysaccharide Endotoxins" Annual Review Biochemistry (2002) pp. 635-700, vol. 71.

Zhou, Z. et al., "Function of *Escherichia coli* MsbA, an Essential ABC Family Transporter, in Lipid A and Phospholipid Biosynthesis" The Journal of Biological Chemistry (1998) pp. 12466-12475, vol. 273, No. 20, issue of May 15.

Cognet, I. et al., "Expression of Recombinant Proteins in a Lipid A Mutant of *Escherichia coli* BL21 with a Strongly Reduced Capacity to Induce Dendritic Cell Activation and Maturation" Joural of Immunological Methods (2003) pp. 199-210, vol. 272.

Vorachek-Warren, M.K. et al., "A Triple Mutant of *Escherichia coli* Lacking Secondary Acyl Chains on Lipid A" The Journal of Biological Chemistry (Apr. 19, 2002) pp. 14194-14205, vol. 277, No. 16.

Japanese Official Action mailed Jun. 2, 2011 issued in related Japanese Patent Application No. 2008-551397.

Lane  1  2  3

A.

B.

US 8,303,964 B2

VIABLE NON-TOXIC GRAM-NEGATIVE BACTERIA

The present application claims priority to U.S. Provisional Application 60/760,314, filed Jan. 19, 2006, incorporated by reference herein in its entirety.

This invention was made with government support under Grant No. GM53609 awarded by the National Institutes of Health.

FIELD OF THE INVENTION

The present invention provides non-toxic Gram-negative bacteria. In particular, the present invention provides viable Gram-negative bacteria (e.g., *E. coli*) substantially lacking lipopolysaccharide (LPS, endotoxin) within the outer membrane. The present invention further provides methods of generating viable non-toxic Gram-negative bacteria and uses thereof. The present invention also provides compositions and methods for inducing immune responses and for researching and developing therapeutic agents.

BACKGROUND OF THE INVENTION

Lipopolysaccharide (LPS, endotoxin) is the major antigen of Gram-negative bacteria. LPS is a glycophospholipid consisting of an antigenic, variable size, carbohydrate chain covalently linked to lipid A, the conserved hydrophobic region structurally defined as N,O-acyl beta-1,6-D-glucosamine 1,4'-bisphosphate. Toxicity of LPS is expressed by lipid A through the interaction with B-cells and macrophages of the mammalian immune system, a process leading to the secretion of proinflammatory cytokines, mainly TNF, which may have fatal consequences for the host. Lipid A also activates human T-lymphocytes (Th-1) "in vitro" as well as murine CD4+ and CD8+ T-cell "in vivo", a property which allows the host's immune system to mount a specific, anamnestic IgG antibody response to the variable-size carbohydrate chain of LPS. On these bases, LPS has been recently recognized as a T-cell dependent antigen "in vivo".

In order to fully express toxicity, LPS must retain its supramolecular architecture, through the association of several units of glycophospholipid monomers forming the lipid A structure. This conformational rearrangement of the molecule is also fundamental for full expression of the immunogenic characteristic.

Sepsis and septic shock are well defined clinical conditions that are caused by bacteria and by LPS, which is the endotoxin elaborated by the bacteria responsible for the above-mentioned pathologies.

The clinical signs of sepsis and septic shock vary, depending on the amount of endotoxin present and the time elapsed in the disease process. The earliest clinical signs of an infection may be fever, mild depression, and lack of appetite. Further into the disease process, the patient will exhibit more obvious signs of shock, including increased heart rate, weak pulse pressure, dehydration, darkening of the gums, cold feet and ears, below-normal temperature, increased respiratory rate, or diarrhea. Once a patient has exhibited signs of endotoxic shock, it should be considered an emergency and a physician should be contacted immediately.

Despite the judicious use of antibiotics and other therapeutic measures, mortality from endotoxin related disorders remains a significant problem. Antibiotic resistance of bacteria, severity of the underlying diseased processes, and inadequate administration of supportive therapy account in part for the failure of conventional treatments. What is needed is an improved understanding of the Gram-negative bacteria that cause endotoxin related disorders. Additionally, improved treatment for endotoxin related disorders are needed.

SUMMARY OF THE INVENTION

The present invention provides non-toxic Gram-negative bacteria. In particular, the present invention provides viable Gram-negative bacteria (e.g., *E. coli*) substantially lacking lipopolysaccharide (LPS, endotoxin) within the outer membrane. The present invention further provides methods of generating viable non-toxic Gram-negative bacteria and uses thereof. The present invention also provides compositions and methods for inducing immune responses and for researching and developing therapeutic agents.

Embodiments of the present invention provide a wide range of method and composition employing Gram-negative bacteria (e.g., *E. coli*) lacking an LPS. Exemplary embodiments are described below in the Summary of the Invention, the Detailed Description of the Invention and the Examples section below. The present invention is not limited to these exemplary embodiments. The Gram-negative bacteria lacking LPS may be generated by any mechanism. A diverse variety of different mechanisms for generating such bacteria are described herein. For example, in some embodiments, genes are mutated (e.g., so as to reduce or eliminate expression of functional protein) that are involved in KDO synthesis. In some embodiments, genes are mutated that are involved in association of KDO with Lipid $IV_A$. In some embodiments, genes are mutated that are involved in Lipid $IV_A$ synthesis. In some embodiments, other genes involved in LPS production or presentation are mutated. The present invention is not limited to gene mutation. In some embodiments, expression is altered using RNA interference or other techniques. In some embodiments, protein function is altered by providing inhibitors (e.g., synthetic or natural competitive or non-competitive ligands, antibodies, etc.). In some embodiments, modified bacteria are further supplied with nutrients, other modifications, or other components useful for maintaining health, growth, etc. in view of the alterations made to affect LPS status. Embodiments of the present invention are not limited to these mechanisms unless specified otherwise. The present invention demonstrates that bacteria lacking LPS are viable, may be made through a variety of routes, and find use in a variety of settings.

The LPS layer is essential to both the form and function of the outer membrane of Gram-negative bacteria. In addition to being a main mediator of Gram-negative pathogenesis, an LPS (endotoxin) structure consisting of at least $KDO_2$-lipid A [2-keto 3-deoxy-D-manno-octulosonate (KDO)] has long been recognized as the minimal structure necessary in *Escherichia coli* for sustained growth.

In some embodiments, the present invention provides a viable Gram-negative bacterial strain lacking KDO despite exclusively elaborating the endotoxically inactive LPS precursor lipid $IV_A$, a known antagonist of LPS-induced sepsis in humans. In some embodiments, the present invention provides viable Gram-negative bacteria lacking D-arabinose 5-phosphate isomerase (API) expression. In some embodiments, the viable Gram-negative bacteria comprises mutations such that the strain is substantially free of KDO. In some embodiments, the mutations include one or more mutations in one or more genes involved in KDO synthesis or modification. In some embodiments, the viable Gram-negative bacteria comprises mutations wherein the mutations prevent association between $KDO_2$ and Lipid $IV_A$ in the LPS biosynthetic pathway, such that Lipid IV$_A$ alone is transported to the outer membrane. In some embodiments, one or more mutations in KDO synthesis genes, or one or more mutations in the LPS biosynthetic pathway, include mutations in, but not limited to, the genes gutQ, kdsD (yrbH), kdsA, kdsB, waaA, msbA, and yhjD, or any other biosynthetic, processing, or trafficking gene. In some embodiments, the strain lacks or substantially lacks synthesis of KDO proteins. In some embodiments, the Outer membrane of the viable Gram-negative bacteria expresses lipid IVa. In some embodiments, the Gram-negative bacteria is E. coli.

In certain embodiments, the present invention provides a method of producing lipid IVa, comprising extracting lipid IVa from viable Gram-negative bacteria.

In certain embodiments, the present invention provides a method of treating an endotoxin related disorder, comprising administering to a subject with an endotoxin related disorder a composition comprising lipid IVa isolated from Gram-negative bacteria.

In certain embodiments, the present invention provides an outer membrane vaccine or other composition for inducing an immune response against a Gram-negative bacteria, the compositions comprising an outer membrane of viable Gram-negative bacteria of the invention. Such compositions may be used to induce immune responses in research, drug-screening, and therapeutic settings.

In certain embodiments, the present invention provides an adjuvant comprising lipid IVa isolated from Gram-negative bacteria.

In certain embodiments, the present invention provides viable Gram-negative bacteria lacking expression of one or more genes of gutQ, kdsD (yrbH), kdsA, kdsB, waaA, msbA, and/or yhjD, or expression of any other biosynthetic, processing, or trafficking genes associated with outer membrane LPS presentation. The bacteria of the invention, or portions thereof (e.g., membrane fractions) find use in research and therapeutic applications.

BRIEF DESCRIPTION OF THE DRAWINGS

FIG. 1A: Inner core-lipid A sugar composition of LPS from phenol extract post-dialysis. GlcN-D-glucosamine; KDO-2-keto 3-deoxy-D-manno-octulosonate; L-glycero-D-manno-heptose-heptose. FIG. 1B: SDS-PAGE analysis of LPS from proteinase K treated whole-cell lysates. Top panel was silver stained, while middle and bottom panels are immunoblots developed using the mAB A6 directed against the nonglycosylated 1,4'-bisphosphorylated β-1,6-linked GlcN disaccharide backbone of lipid A. The middle panel membrane was treated with 1% acetic acid to release lipid A prior to immunological reactions. Lanes 1-5 are Salmonella enterica serovar reference strains of different LPS chemotypes [1. 3749 (Ra); 2. 3750 (Rb2); 3. 3748 (Rb3); 4. 3769 (Rd1), 5. 1102 (Re)], 6. wild-type BW30270, 7. KPM22, 8. KPM25, 9. KPM22 with A5P in the growth media, 10. KPM31, 11. KPM34, 12. KPM31 with A5P in the growth media, 13. KPM40, 14. KPM42, 15. KPM40 with A5P in the growth media, 16. 200 ng of chemically synthesized lipid IVa (compound 406).

FIG. 2A: BW30270 (inset isotopic distribution of glycoform I; 3915.71 u). FIG. 2B: KPM22 (inset structure of lipid IVa; 1404.86 u). FIG. 2C: KPM25 (inset Wild-type LPS with chemical structure of KDO$_2$-lipid A (Re endotoxin) depicted and heptose attachment point indicated by arrow. Red, blue, and green peak labels correspond to the peak families of glycoforms I, IV, and II, respectively (see, e.g., S. Müller-Loennies, B. Lindner, H. Brade, J. Biol. Chem. 278, 34090 (2003); herein incorporated by reference in its entirety). Individual structure peak assignments are listed in Table 9. PE—phosphatidylethanolamine; P—phosphate; P-EtN—phosphoethanolamine; $LA_{tri}$, $LA_{tetra}$, $LA_{penta}$, $LA_{hexa}$—acylation state of lipid A.

FIG. 5A: Colanic acid production estimated as µg of methylpentose (L-fucose) per mL per OD of culture of suspended cells. FIG. 5B: Immunoblot of enterobacterial common antigen (ECA) using the mAb 898 antibody. Lane 1 (BW30270), Lane 2 (KPM22), Lane 3 (KPM25).

DEFINITIONS

Figure 1:
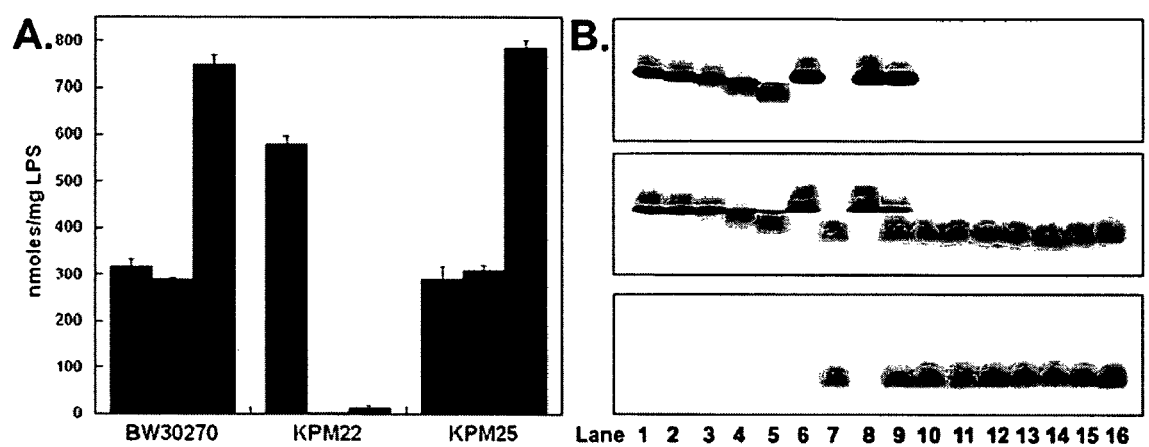
FIG. 1 presents characterization of LPS samples extracted from KPM22.

To facilitate understanding of the invention, a number of terms are defined below.

As used herein, the terms "subject" and "patient" refer to any animal, such as a mammal like a dog, cat, bird, livestock, and preferably a human.

As used herein, the terms, "LPS related disorder", "condition associated with endotoxin", "endotoxin associated disorder", "endotoxin-related disorder", "sepsis", "sepsis related disorder", or similar terms, describes any condition associated with LPS, e.g., a condition associated with bacteremia or introduction of lipopolysaccharide into the blood stream or onto an extra-gastrointestinal mucosal surface (e.g., the lung). Such disorders include, but are not limited to, endotoxin-related shock, endotoxin-related disseminated intravascular coagulation, endotoxin-related anemia, endotoxin-related thrombocytopenia, endotoxin-related adult respiratory distress syndrome, endotoxin-related renal failure, endotoxin-related liver disease or hepatitis, systemic immune response syndrome (SIRS) resulting from Gram-negative infection, Gram-negative neonatal sepsis, Gram-negative meningitis, Gram-negative pneumonia, neutropenia and/or leucopenia resulting from Gram-negative infection, hemodynamic shock and endotoxin-related pyresis.

The term, "viable non-toxic Gram-negative bacteria" refers to a viable Gram-negative bacterial strain comprising an outer membrane substantially free of LPS.

The terms "cells" and "host cells" and "recombinant host cells", which are used interchangeably herein, refer to cells that are capable of or have been transformed with a vector, typically an expression vector. The host cells used herein are preferably Gram-negative bacteria. It is understood that such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The term "culture medium" is recognized in the art, and refers generally to any substance or preparation used for the cultivation of living cells.

The term "derived from," as used, for example, in the context of deriving lipid IVa from a strain of Gram-negative bacteria, refers to lipid IVa that can be obtained from the bacteria or the protein, and is intended to include fragments or portions of proteins.

The term "defective" as used herein, with regard to a gene or gene expression, means that the gene is not a wildtype gene and that the organism does not have a wildtype genotype and/or a wildtype phenotype. The defective gene, genotype or phenotype may be the consequence of a mutation in that gene, or of a gene that regulates the expression of that gene (e.g., transcriptional or post-transcriptional), such that its normal expression is disrupted or extinguished. "Disrupted gene expression" is intended to include both complete inhibition and decreased gene expression (e.g., as in a leaky mutation), below wildtype gene expression.

The term "Gram-negative bacteria" is recognized in the art, and refers generally to bacteria that do not retain Gram stain (e.g., the deposition of a colored complex between crystal violet and iodine). In an exemplary Gram stain, cells are first fixed to a slide by heat and stained with a basic dye (e.g., crystal violet), which is taken up by all bacteria (i.e., both Gram-negative and Gram-positive). The slides are then treated with an iodine-KI mixture to fix the stain, washed with acetone or alcohol, and finally counterstained with a paler dye of different color (e.g., safranin). Gram-positive organisms retain the initial violet stain, while Gram-negative organisms are decolorized by the organic solvent and hence show the counterstain. Exemplary Gram-negative bacteria and cell lines include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., *Corynebacteria* spp., *Citrobacter* spp., *Chlamydia* spp., *Brucella* spp., *Pseudomonas* spp., *Helicobacter* spp. and *Vibrio* spp.

The term "mutant Gram-negative bacteria" "LPS mutant Gram-negative bacteria", "kdsD and gutQ mutant Gram-negative bacteria", "API mutant Gram-negative bacteria" or similar terms, as used herein, includes Gram-negative bacteria of the invention that have been mutated one or more times in, for example, one or more of the gutQ, kdsD, kdsA, kdsB, waaA, msbA, yhjD genes, of any other biosynthetic, processing, or trafficking gene thereby producing an outer membrane substantially lacking LPS protein expression.

An "immunogenic portion of a molecule" refers to a portion of the molecule that is capable of eliciting an immune reaction against the molecule in a subject.

The term "isolated" as applied to LPS or lipid IVa molecules, refers to LPS or lipid IVa which has been isolated (e.g., partial or complete isolation) from other bacterial components, in particular from the outer membrane.

As used herein, the term "portion" when used in reference to a sequence (e.g., an amino acid sequence of a protein, a nucleic acid sequence of a gene) represents any amount of the referenced sequence (e.g., 0.001%, 0.1%, 1%, 10%, 30%, 50%, 75%, 80%, 85%, 90%, 95%, 98%, 99.999% of an amino acid sequence or nucleic acid sequence).

The term "modulation" as used herein refers to both upregulation (i.e., activation or stimulation (e.g., by agonizing or potentiating)) and downregulation (i.e., inhibition or suppression (e.g., by antagonizing, decreasing or inhibiting)). The term "inducible" refers in particular to gene expression which is not constitutive but which takes place in response to a stimulus (e.g., temperature, heavy metals or other medium additive).

The term "non-human animals" includes any animal that can be treated or used in testing the present invention, including mammals such as non-human primates, rodents, sheep, dogs, cows, pigs, chickens, as well as amphibians, reptiles, etc. Preferred non-human animals are selected from the primate family or rodent family (e.g., rat and mouse).

The term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

The term "pharmaceutically acceptable" means a material that is not biologically or otherwise undesirable, i.e., the material may be administered to an individual along with the selected compound without causing any undesirable biological effects or interacting in a deleterious manner with any of the other compounds of the pharmaceutical composition in which it is contained.

The term "pyrogenic" or "pyrogenicity" refers to the ability of a compound to induce fever or a febrile response when administered to a subject. Such febrile responses are generally mediated by the host proinflammatory cytokines IL-1, IL-6 and/or TNF-α, the secretion of which is induced, e.g., by LPS.

A substance having "reduced pyrogenicity" or a "reduced pyrogenic derivative" refers to a substance having less pyrogenic activity than the counterpart substance, e.g., less than about 80% pyrogenic relative to a counterpart substance, preferably less than about 70% pyrogenic, more preferably less than about 60% pyrogenic, more preferably less than about 50° pyrogenic, more preferably less than about 40% pyrogenic, and even more preferably less than about 30% pyrogenic. In other terms, a substance having reduced pyrogenicity is at least about 20%, 30%, 40%, 50%, 60%, or 70% less pyrogenic than the corresponding substance as determined by any of the assays described herein or known in the art.

"Substantially reduced pyrogenicity" or "substantially reduced pyrogenic derivative" refers to a substance (e.g., produced by viable non-toxic Gram-negative bacteria) which has been altered such that it has less than 20% pyrogenicity relative to the wildtype substance, preferably less than 10% pyrogenicity, preferably less than 1% pyrogenicity, preferably less than $10^{-1}$% pyrogenicity, preferably less than $10^{-2}$% pyrogenicity, preferably less than $10^{-3}$% pyrogenicity, preferably less than $10^{-4}$% pyrogenicity, preferably less than $10^{-5}$% pyrogenicity, and most preferably less than $10^{-6}$% pyrogenicity relative to the wildtype substance. In other terms, a substance that has substantially reduced pyrogenicity is at least about 90%, 99%, 10 fold, about $10^{-2}$ fold, about $10^{-3}$ fold, at least about $10^{-4}$ fold, at least about $10^{-5}$ fold, at least about $10^{-6}$ fold less pyrogenic relative to the corresponding unaltered substance as determined by any of the assays described herein or known in the art.

As used herein, the term "transfection" means the introduction of a nucleic acid (e.g., via an expression vector) into a recipient cell by nucleic acid-mediated gene transfer.

"Transformation", as used herein, refers to a process in which a cell's genotype is changed as a result of the cellular uptake of exogenous DNA or RNA. In an illustrative embodiment, a transformed cell is one that expresses a mutant form of one or more of the kdsD and gutQ genes. A transformed cell can also be one that expresses a nucleic acid that interferes with the expression of an gutQ, kdsD, kdsA, kdsB, waaA, msbA, ynjD gene of any other biosynthetic, processing, or trafficking gene.

As used herein, the term "transgene" means a nucleic acid (e.g., a mutant kdsD, gutQ, kdsA, kdsB, waaA, msbA, ynjD gene of any other biosynthetic, processing, or trafficking gene, or an antisense transcript thereto) that has been introduced into a cell. A transgene could be partly or entirely heterologous, i.e., foreign, to the transgenic animal or cell into which it is introduced, or, can be homologous to an endogenous gene of the organism or -cell into which it is introduced, but which is designed to be inserted, or is inserted, into the animal or cell's genome in such a way as to alter the genome of the cell into which it is inserted. A transgene can also be present in a cell in the form of an episome.

The term "treating" a subject for a condition or disease, as used herein, is intended to encompass curing, as well as ameliorating at least one symptom of the condition or disease.

The term "vector" refers to a nucleic acid molecule, which is capable of transporting another nucleic acid to which it has been linked. Vectors capable of directing the expression of genes to which they are operatively linked are referred to herein as "expression vectors." The term "expression system" as used herein refers to an expression vector under conditions whereby an mRNA may be transcribed and/or an mRNA may be translated into protein, structural RNA, or other cellular component. The expression system may be an in vitro expression system, which is commercially available or readily made according to art known techniques, or may be an in vivo expression system, such as a eukaryotic or prokaryotic cell containing the expression vector. In general, expression vectors of utility in recombinant DNA techniques are often in the form of "plasmids" which refer generally to circular double stranded DNA loops that, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and are well known in the art or which become known in the art subsequently hereto (e.g., cosmid, phagemid and bacteriophage vectors).

DETAILED DESCRIPTION OF THE INVENTION

The present invention provides non-toxic Gram-negative bacteria. In particular, the present invention provides viable Gram-negative bacteria (e.g., *E. coli*) substantially lacking lipopolysaccharide (LPS, endotoxin) within the outer membrane. The present invention further provides methods of generating viable non-toxic Gram-negative bacteria and uses thereof. The present invention also provides compositions and methods for inducing immune responses and for researching and developing therapeutic agents.

Gram-negative bacteria possess an asymmetric lipid bilayer that surrounds the peptidoglycan, the outer membrane (OM). The OM inner leaflet is primarily composed of various glycerophospholipids, whereas the outer leaflet predominantly contains the unique amphiphilic macromolecule, lipopolysaccharide (LPS). In *Escherichia coli* and other closely related enteric bacteria, there are ~$10^6$ LPS molecules per cell covering nearly 75% of the total cell surface area, accounting for ~30% of the OM gross weight (see, e.g., S. M. Galloway, C. R. Raetz, J. Biol. Chem. 265, 6394 (1990); L. Leive, Ann. N.Y. Acad. Sci. 235, 109 (1974); H. Nikaido, in *Escherichia coli* and *Salmonella typhimurium*: cellular and molecular biology, F. C. Neidhardt, Ed. (American Society for Microbiology, Washington, D.C., 1987), vol. 1, pp. 29-47; each herein incorporated by reference in their entireties). The exposed location at the interface between the bacterial cell and the aqueous environment presents LPS as a main OM-associated surface antigen. LPS is involved in a diverse spectrum of pathological and physiological activities associated with the host immune response (see, e.g., A. Wiese, et al., Biol. Chem. 380, 767 (1999); H. Heine, et al., Mol. Biotechnol. 19, 279 (2001); each herein incorporated by reference in their entireties). LPS is an immunostimulatory/inflammatory molecule recognized as a mediator of Gram-negative pathogenesis and generalized inflammation, and as such the term endotoxin is often used interchangeably with LPS. The LPS layer is essential to both the form and function of the OM of Gram-negative bacteria. Thus, in addition to being a key player in Gram-negative pathogenesis, LPS is also a critical determinant of the survival of the bacterium.

LPS of various Gram-negative bacteria conform to a common structural architecture conceptually divided into three regions: the OM-embedded lipid A, an oligosaccharide core, followed by an O-specific hydrophilic polysaccharide chain consisting of n-repeat units in Enterobacteriaceae or short branched oligosaccharides in certain bacteria, comprising human mucosal pathogens such as *Neisseria meningitis, N. gonorrhoeae, Haemophilus influenzae, Bordetella pertussis*, and *Chlamydia* spp. Lipid A is the most conserved LPS domain amongst Gram-negative bacterial genera, and being the structural component responsible for the biological activities within the host, represents an endotoxic principle of LPS. In enteric bacteria, lipid A consists of a β-1,6-linked D-glucosamine disaccharide backbone which is acylated with four (R)-3-hydroxy-myristic acids in ester-(3,3') or amide-(2,2') linkages. Mature lipid A molecules of *E. coli* wild-type strains typically contain two additional acyl chains, primarily laurate and myristate, attached to the (R)-3-hydroxymyristoyl group of the nonreducing glucosamine to form the characteristic acyloxyacyl units of lipid A. The oligosaccharide core connects lipid A to the hypervariable polysaccharide chain, and is further divided into the inner and outer oligosaccharide core regions. Whereas the outer core is less well conserved, varying both in saccharide composition and glycosidic linkages, the majority of Gram-negative bacteria elaborate an inner core containing at least one 2-keto 3-deoxy-D-manno-octulosonate (KDO) molecule.

KDO is an essential component of LPS that is a conserved residue found in nearly all LPS structures (see, e.g., O. Hoist, Trends Glycosci. Glycotechnol. 14, 87 (2002); herein incorporated by reference in its entirety). The minimal LPS structure required for growth of *E. coli* is two KDO residues attached to lipid A ($KDO_2$-lipid A or Re endotoxin) (see, e.g., C. R. Raetz, C. Whitfield, Annu. Rev. Biochem. 71, 635 (2002); S. Gronow, H. Brade, J. Endotoxin Res. 7, 3 (2001); each herein incorporated by reference in their entireties), emphasizing the importance of KDO in maintaining the integrity and viability of the bacterial cell. L-API is encoded by the kdsD gene in *E. coli* K-12 (see, e.g., Meredith, T. C. & Woodard, R. W. (2003) J Biol Chem 278, 32771-7; herein incorporated by reference in its entirety).

Figure 11:
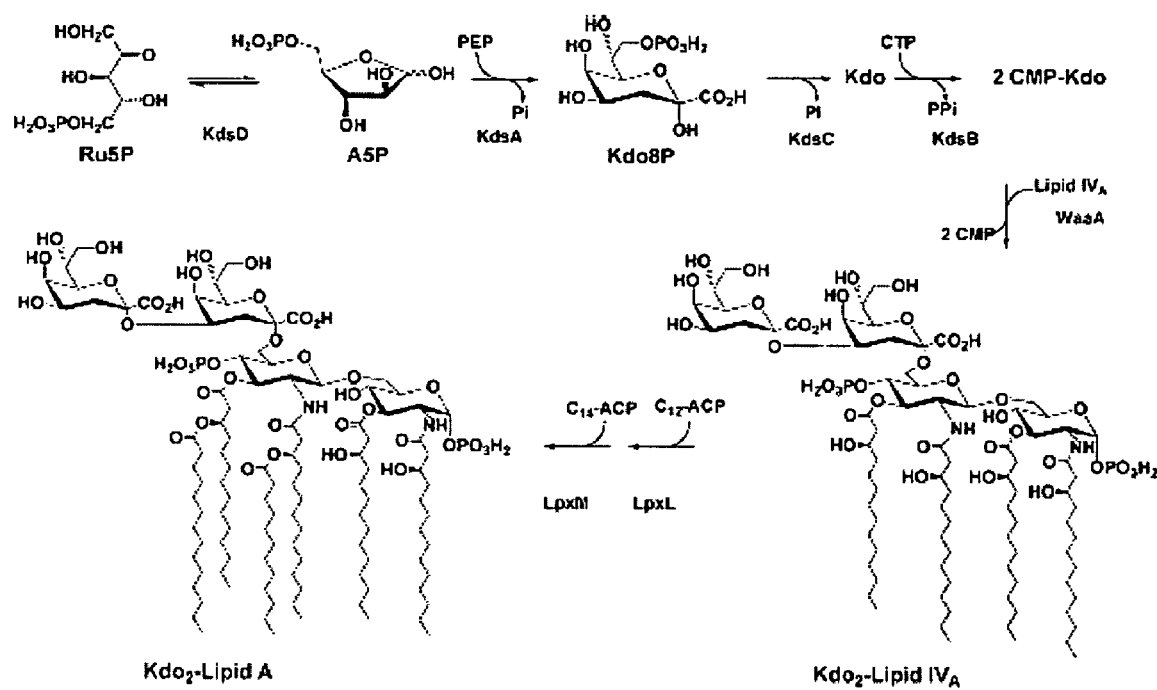
FIG. 11 shows the biosynthesis and incorporation of Kdo into LPS. Enzymes involved are (1) D-arabinose 5-phosphate isomerase (KdsD/GutQ), (2) Kdo8P synthase (KdsA), (3) Kdo8P phosphatase (KdsC), and (4) CMP-Kdo synthetase (KdsB). In *E. coli*, two molecules of activated Kdo are then sequentially transferred to lipid $IV_A$ by (5) Kdo transferase (WaaA) before the stepwise addition of the secondary acyl chains (6) laurate (LpxL) and (7) myristate (LpxM).

The ubiquitous nature of KDO within LPS structures has prompted investigation into its biosynthesis. The pathway is initiated by the enzyme d-arabinose 5-phosphate (A5P) isomerase (API), which converts the pentose pathway intermediate D-ribulose 5-phosphate into A5P. Subsequently, A5P is condensed with phosphoenolpyruvate to form Kdo 8-phosphate (Kdo8P) (KdsA), hydrolyzed to Kdo (KdsC), activated as the sugar nucleotide CMP-Kdo (KdsB), before finally being transferred from CMP-Kdo to the acceptor lipid IVA (WaaA) (FIG. 11). The late acyltransferases LpxL and LpxM next transfer the fatty acids laurate and myristate, respectively, to Kdo2-lipid IVA to form the characteristic acyloxyacyl units of hexaacylated Kdo-lipid A. In *E. coli* K-12, there are two API genes (kdsD and gutQ).

Figure 10:
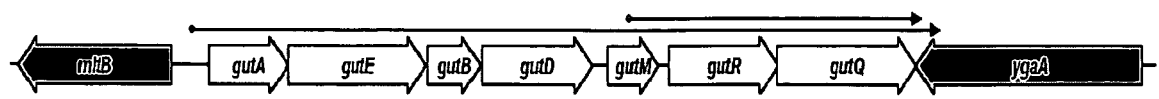
FIG. 10 shows the gut operon of *E. coli* K-12 MG1655. Transcription initiation sites were determined using reverse transcriptase mapping by Yamada and Saier (see, e.g., Yamada, M. & Saier, M. H., Jr. (1988) J Mol Biol 203, 569-83; herein incorporated by reference in its entirety), and are indicated by arrows.

It was speculated that other APIs may exist in *E. coli* based on homology searches. In particular, the final open reading of the glucitol operon gutQ has significant homology (45% identity) to kdsD (formerly yrbH). G-API is the last gene product of the gutAEBDMRQ operon, which contains seven convergently transcribed genes (FIG. 10). As shown in Table 1, gutQ and kdsD share similar biochemical properties.

TABLE 1

Biochemical Properties of kdsD and gutQ

| Property | kdsD[a] | gutQ |
|---|---|---|
| $K_m$ (A5P) | 0.61 ± 0.06 mM | 1.2 ± 0.1 mM |
| $K_m$ (Ru5P) | 0.35 ± 0.08 mM | 0.64 ± 0.08 mM |
| $k_{cat}$ (A5P to Ru5P) | 157 ± 4 sec$^{-1}$ | 218 ± 4 sec$^{-1}$ |
| $k_{cat}$ (Ru5P to A5P) | 255 ± 16 sec$^{-1}$ | 242 ± 11 sec$^{-1}$ |
| $K_{eq}$ (calc.)[b] | 0.47 (0.35) | 0.47 (0.48) |
| Optimum pH | 8.4 | 8.25 |
| Specific for A5P/Ru5P [c] | Yes | Yes |
| Equiv. of $Zn^{2+}$/subunit [d] | 1.0 ± 0.1 | 1.4 ± 0.2 |
| Inhibition by 10 μM $Zn^{2+}$ [e] | Yes | Yes |
| Activation by EDTA [f] | Yes | Yes |
| Subunit MW (calc.) [g] | 35104 Da (35196 Da) | 33909 Da (34031 Da) |
| Native MW [h] | 122 ± 5 kDa (tetramer) | 133 ± 4 kDa (tetramer) |

[a] Data from Yamada, M., Yamada, Y. & Saier, M. H., Jr. (1990) DNA Seq 1, 141-5; herein incorporated by reference in its entirety
[b] Measured by 31P NMR; calculated from Haldane relationship (Ru5P/A5P)
[c] See experimental procedures for tested substrates
[d] Equivalents of $Zn^{2+}$ per monomer as determined by high-resolution inductively coupled plasma-mass spectrometry
[e] Less than 5% activity remaining
[f] As isolated enzyme with 10 μM EDTA
[g] Determined by electrospray ionization mass spectrometry; calculated from protein sequence
[h] Determined by gel filtration The glucitol operon expresses a phosphoenolpyruvate:sugar phosphotransferase system (PTS) that is responsible for the coordinated uptake and catabolism of D-glucitol from the environment (see, e.g., T. C. Meredith, R. W. Woodard, J. Biol. Chem. 278, 32771 (2003); herein incorporated by reference in its entirety). The operon was originally studied by Lengeler (see, e.g., C. Galanos, et al., Eur. J. Biochem. 9, 245 (1969); S. Müller-Loennies, et al., J. Biol. Chem. 278, 34090 (2003); each herein incorporated by reference in their entireties) and subsequently by Saier (see, e.g., K. A. Brozek, C. R. Raetz, J. Biol. Chem. 265, 15410 (1990); H. Nikaido, Microbiol. Mol. Biol. Rev. 67, 593 (2003); each herein incorporated by reference in their entireties), and is known to consist of seven convergently transcribed genes, gutAEBDMRQ. The $EII^{Gut}$ complex is formed by gutA (EIIC1 domain), gutE (EIIBC2 domains), and gutB (EIIA domain), and transports D-glucitol across the inner membrane and into the cell as D-glucitol 6-phosphate. D-Glucitol 6-phosphate is then further metabolized by gutD, an NADH dependent dehydrogenase, to the glycolytic intermediate D-fructose 6-phosphate.

Expression of the gut operon is tightly controlled by a complex multicomponent regulatory system, consisting of a transcriptional repressor (gutR) and a transcriptional activator (gutM) in addition to cAMP-CAP (cyclic adenosine monophosphate-catabolite activator protein) mediated regulation (see, e.g., C. J. Belunis, et al., J. Biol. Chem. 270, 27646 (1995); herein incorporated by reference in its entirety). However, the function of gutQ remains unknown (see, e.g., R. C. Goldman, W. E. Kohlbrenner, J. Bacteriol. 163, 256 (1985); herein incorporated by reference in its entirety).

In experiments conducted during the development of embodiments of the present invention, viable Gram-negative bacteria substantially lacking outer membrane LPS expression were constructed despite exclusively elaborating the endotoxically inactive LPS precursor lipid IVa, a known antagonist of LPS-induced sepsis in humans. The present invention is not limited to particular methods of constructing viable Gram-negative bacteria substantially lacking outer membrane LPS expression (e.g., through suppression of API expression; through mutation of the gutQ and/or kdsD genes; through suppression of KDO expression; through inhibiting associations between KDO and Lipid $IV_A$; through mutations of the kdsA, and/or kdsB, and/or waaA and/or msbA and/or yhjD genes, or other biosynthetic, processing, or trafficking genes; through suppression of lipid $IV_A$ expression; through mutations of the lpxM gene, or other biosynthetic, processing, or trafficking genes for lipid $IV_A$).

The present invention contemplates the use of any type of Gram-negative bacterial strain in the construction of viable Gram-negative bacteria substantially lacking outer membrane LPS expression. Examples of Gram-negative bacteria useful in the present invention include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., *Corynebacteria* spp., *Citrobacter* spp., *Chlamydia* spp., *Brucella* spp., *Pseudomonas* spp., *Helicobacter* spp. and *Vibrio* spp. In preferred embodiments, *Escherichia coli* is used. Examples of *Escherichia* strains which can be used include, but are not limited to, *Escherichia coli* (*E. coli*) strains DH5a, HB 101, HS-4, 4608-58, 1-184-68, 53638-C-17, 13-80, and 6-81 (see, e.g., Sambrook, et al., (Eds.), 1993, In: Molecular Cloning, Cold Spring Harbor Press, Cold Spring Harbor, N.Y.); Grant, et al., 1990, Proc. Natl. Acad. Sci., USA, 87:4645; Sansonetti, et al., 1982, Ann. Microbiol. (Inst. Pasteur), 132A:351), enterotoxigenic *E. coli* (Evans, et al., 1975, Infect. Immun., 12:656), enteropathogenic *E. coli* (Donnenberg, et al., 1994, J. Infect. Dis., 169:831; each herein incorporated by reference in their entireties) and enterohemorrhagic *E. coli* (see, e.g., McKee and O'Brien, 1995, Infect. Immun., 63:2070).

The present invention is not limited to specific culture conditions for the growth of mutant Gram-negative bacterial strains (e.g., Gram-negative bacterial strains with mutations in the kdsD and/or gutQ, kdsA, kdsB, waaA, msbA, ynjD genes, or other biosynthetic, processing, or trafficking genes). For illustrative purposes, bacteria can be grown in any standard liquid medium suitable for bacterial growth, such a LB medium (Difco, Detroit Mich.), Nutrient broth (Difco), Tryptic Soy broth (Difco), or M9 minimal broth (Difco), using conventional culture techniques that are appropriate for the bacterial strain being grown (Miller, 1991, supra). As an alternative, the bacteria can be cultured on solid media such as L-agar (Difco), Nutrient agar (Difco), Tryptic Soy agar (Difco), or M9 minimal agar (Difco). For Gram-negative bacterial strains wherein said strain comprises the mutations kdsD and/or gutQ, an exogenous D-arabinose 5-phosphate source is used for bacterial growth and survival (Meredith et al., 2006, ACS Chem. Biol. 1:33-42; incorporated herein by reference in its entirety). Alternatively, experiments conducted during the development of some embodiments of the invention show that overexpression of the msbA gene in strains comprising the kdsD and/or gutQ mutations is an alternative to supplementation by D-arabinose 5-phosphate for bacterial growth and survival.

In some embodiments, the present invention provides viable Gram-negative bacteria with mutations in the gutQ, kdsD (yrbH), kdsA, kdsB, waaA, msbA, and/or yhjD genes, or mutations in any other biosynthetic, processing, or trafficking gene. In some embodiments, mutations of the gutQ and kdsD genes inhibit API expression within the bacterial strain, which inhibits KDO expression, which inhibits outer membrane LPS expression. In some embodiments, the present invention provides viable Gram-negative bacteria with mutations in the kdsA gene. In some embodiments, the present invention provides viable Gram-negative bacteria with mutations in the kdsB gene. In some embodiments, the present invention provides viable Gram-negative bacteria with mutations in the waaA gene. Experiments conducted during the development of the embodiments of the present invention showed that mutations of kdsA, kdsB, and/or waaA inhibit the LPS biosynthetic pathway by preventing production of KDO or association between $KDO_2$ and Lipid $IV_A$ such that Lipid $IV_A$ alone is transported to the outer membrane. The bacterial cells survive and are LPS free and non-toxic. In some embodiments, the present invention provides viable Gram-negative bacteria with mutations in the gutQ, kdsD, kdsA, kdsB, and/or waaA genes, and further comprises a mutation in the msbA gene. In some embodiments the present invention provides viable Gram-negative bacteria with mutations in the gutQ, kdsD, kdsA, kdsB, or waaA genes, and further comprises a mutation in the yhjD gene.

The present invention contemplates the use of any technique for introducing genetic mutations within Gram-negative bacteria. Such techniques include, but are not limited to, non-specific mutagenesis, using chemical agents such as N-methyl-N'-nitro N-nitrosoguanidine, acridine orange, ethidium bromide, or non-lethal exposure to ultraviolet light (see, e.g., Miller (Ed.), 1991, In: A Short Course in Bacterial Genetics, Cold Spring Harbor Press, Cold Spring Harbor, N.Y.; herein incorporated by reference in its entirety). Alternatively, the mutations can be introduced using Tn10 mutagenesis, bacteriophage-mediated transduction, lambda phage-mediated allelic exchange, or conjugational transfer, or site directed mutagenesis using recombinant DNA techniques (see, e.g., Miller (Ed.), 1991, supra; Hone, et al., 1987, J. Infect. Dis., 156:167; Noriega, et al, 1994, Infect. Immun., 62:5168; Hone, et al., 1991, Vaccine, 9:810; Chatfield, et al., 1992, Vaccine, 10:53; Pickard, et al., 1994, Infect. Immun., 62:3984; Odegaard, et al., 1997, J. Biol. Chem., 272:19688; Lee, et al., 1995, J. Biol. Chem., 270:27151; Garrett, et al., 1998, J. Biol. Chem., 273:12457; each herein incorporated by reference in their entireties). Any method for introducing mutations may be used and the mutations can be introduced in conjunction with one or more additional mutations. For example, in some embodiments the present invention provides viable Gram-negative bacteria with more than one mutation such as mutations in the gutQ, kdsD, kdsA, kdsB, waaA msbA, yhjD genes, or mutations in any other biosynthetic, processing, or trafficking gene.

In some embodiments, mutations within Gram-negative bacteria (e.g., mutations of the gutQ, kdsD (yrbH), kdsA, kdsB, waaA, msbA, and/or yhjD genes, or mutations of any other biosynthetic, processing, or trafficking genes) are either constitutively expressed or under the control of inducible promoters, such as, for example, the temperature sensitive heat shock family of promoters, or the anaerobically-induced nirB promoter (see, e.g., Harborne, et al., 1992, Mol. Micro., 6:2805; herein incorporated by reference in its entirety) or repressible promoters, such as uapA (see, e.g., Gorfinkiel, et al., 1993, J. Biol. Chem., 268:23376; herein incorporated by reference in its entirety) or gcv (see, e.g., Stauffer, et al., 1994, J. Bact, 176:6159; herein incorporated by reference in its entirety). Selection of an appropriate promoter will depend on the host bacterial strain and will be obvious to those skilled in the art.

In some embodiments, the present invention provides viable Gram-negative bacteria (e.g., *E. coli*) lacking API expression. The present invention is not limited to a particular method of inhibiting API expression. In some embodiments, API expression is inhibited through suppression of KDO protein expression. The present invention is not limited to a particular method of suppressing KDO protein expression. In some embodiments, KDO protein expression is suppressed through, for example, mutation of the gutQ gene, kdsD gene, kdsA gene or kdsB gene, or mutations in any other KDO biosynthetic gene.

In some embodiments, the present invention provides viable non-toxic (e.g., endotoxin free) Gram-negative bacteria (e.g., *E. coli*). The present invention is not limited to a particular method of providing viable non-toxic Gram-negative bacteria. In some embodiments, viable non-toxic Gram-negative bacteria are provided through suppression of LPS expression in the outer membrane. The present invention is not limited to a particular method of suppressing LPS expression in the outer membrane. In some embodiments, LPS expression is suppressed through suppression of API protein expression. The present invention is not limited to a particular method of suppressing API expression. In some embodiments, API expression is suppressed through suppression of KDO protein expression. The present invention is not limited to a particular method of suppressing KDO protein expression. In some embodiments, KDO protein expression is suppressed through, for example, mutation of the gutQ gene and the kdsD gene. In some embodiments, KDO protein expression at the outer membrane does not occur due to the KDO protein not associating with Lipid $IV_A$, such that only Lipid $IV_A$ is transported to the outer membrane. For example, mutations in gutQ, kdsD, kdsA, kdsB, waaA msbA, and/or yhjD genes or mutations of any other biosynthetic, processing, or trafficking genes eliminate the formation of or membrane presentation of the $KDO_2$-Lipid $IV_A$ complex, resulting in, for example, only the Lipid $IV_A$ molecule being transported to the outer membrane and no subsequent LPS formation.

In some embodiments, the viable non-toxic Gram-negative bacteria can be genetically engineered via cloning methods known to those skilled in the art (see Sambrook et al., Molecular Cloning; A Laboratory Manual, Cold Spring Harbor Laboratory Press; incorporated herein by reference in its entirety) to express, produce and display non-native proteins and peptides such as, but not limited to, LPS from other bacterial organisms, unique lipid derivatives, human protein or peptide production, non-human protein or peptide production, vaccine production, and the like. Such products produced find utility in a variety of applications, including but not limited to, clinical therapeutics and basic research endeavors.

In some embodiments, the present invention provides viable Gram-negative bacteria (e.g., *E. coli*) comprising an outer membrane expressing lipid IVa. The present invention is not limited to a particular method of providing viable Gram-negative bacteria comprising an outer membrane expressing lipid IVa. In some embodiments, viable Gram-negative bacteria comprising an outer membrane expressing lipid IVa is accomplished through suppression of API protein expression. The present invention is not limited to a particular method of suppressing API protein expression. The present invention is not limited to a particular method of suppressing API expression. In some embodiments, API expression is suppressed through suppression of KDO protein expression. The present invention is not limited to a particular method of suppressing KDO protein expression. In some embodiments, KDO protein expression is suppressed through, for example, mutation of the gutQ, kdsD, kdsA, kdsB, waaA, msbA, and/or yhjD gene or mutations of any other biosynthetic, processing, or trafficking genes. In some embodiments, LPS free viable Gram-negative bacteria comprising an outer membrane expressing Lipid $IV_A$ is accomplished by inhibiting the association between KDO and Lipid $IV_A$, such that only Lipid $IV_A$ is transported to the outer membrane (e.g., without KDO). The present invention is not limited to a particular method of inhibiting the association between KDO and Lipid $IV_A$. In some embodiments, the association of KDO and Lipid $IV_A$ is inhibited by, for example, mutations in the gutQ, kdsD, kdsA, kdsB, waaA, msbA and/or yhjD genes, or any or mutations of any other biosynthetic, processing, or trafficking genes. In some embodiments, the present invention provides lipid IVa isolated from viable non-toxic Gram-negative bacteria (e.g., *E. coli*). Lipid IVa is used, for example, in studying mammalian septic shock signaling pathways, and as a building block in the synthesis of LPS-type molecules. Current methods for isolating lipid IVa involve traditional total organic synthesis, degradation of mature LPS, or purification from conditional mutants that elaborate a heterogeneous LPS layer that contains a fraction of the desired lipid IVa. Drawbacks for such methods include low lipid IVa yield and high amounts of labor. Isolation of lipid IVa from the viable non-toxic Gram-negative bacteria of the present invention represents a significant improvement over such methods due to the outer membrane presence of lipid IVa.

In some embodiments, the present invention provides outer membrane vesicles isolated from viable non-toxic Gram-negative bacteria (e.g., *E. coli*). Lipid IVa is an antagonist of septic shock signaling pathways, and a viable approach to treating patients with acute sepsis is to block the signaling pathway involving LPS. In some embodiments, isolated outer membrane vesicles from viable Gram-negative bacteria comprising an outer membrane expressing lipid IVa are used to treat, or prophylactically prevent, sepsis related disorders. Outer membrane vesicles prepared from the viable non-toxic Gram-negative bacteria of the present invention (e.g., the ΔAPI strain) contain lipid IVa as an LPS antagonist.

In some embodiments, outer membrane vesicles isolated from viable Gram-negative bacteria (e.g., *E. coli*) are used for purposes of improved outer membrane vesicle based vaccines. OMV based vaccines are often "detoxified' by stripping away the LPS by harsh chemical treatments. Stripping methods, however, have a deleterious affect on protein components of the OMV vaccine, which can be good candidates to target antibodies against, particularly of cloned outer membrane proteins from other Gram-negative pathogens. Detoxification would not be necessary with the ΔAPI mutant strain as hosts, providing an additional level of safety.

In some embodiments, the present invention provides Gram-negative bacteria comprising an outer membrane with both lipid IVa and LPS expression. Separating the toxicity of LPS from the immunostimulatory properties is a major challenge to developing LPS based adjuvants or LPS based vaccines. Since the block in the ΔAPI strain is early in the LPS pathway, enzymes from other bacteria (which modify LPS with phosphate groups, ethanolamine, L-4-deoxy arabinose, different acyl chain lengths, etc.) and mutated enzymes with altered activities can be used to generate an array of LPS molecules with unique biological activities inside the cell. Many methods for such genetic manipulations already exist in *Escherichia coli*. Further, mature LPS synthesis can be restored by inclusion of D-arabinose 5-phosphate in the growth media, allowing one to control and optimize the amount and ratio of LPS derivatives to mature LPS. Such LPS "blends" may achieve the desired balance between immunostimulatory activity while retaining acceptable low levels of potential toxicity.

In some embodiments, viable non-toxic Gram-negative bacteria are used as hosts for the production of endotoxin free therapeutic molecules. The present invention is not limited to particular therapeutic molecules. Traditionally, the production of therapeutic molecules in Gram-negative bacteria, whether it be OM vesicles for vaccines, LPS type molecules (such as monophosphoryl lipid A (MPLA)) to be used as adjuvants, recombinant pharmaceutical proteins, macromolecules, or DNA for mammalian cell transfection/gene therapy, is plagued by the presence of endotoxin from the bacterial host. Contamination of the therapeutic molecule with endotoxin is a concern, as the immunogenic potential of LPS is well documented. Current production strategies to alleviate endotoxin contamination include various purification techniques, such as the kits marketed for endotoxin free DNA plasmid purification, followed by assays to measure endotoxin levels. As the ΔAPI strain does not produce endotoxin, such purification steps are not required. As such, the viable non-toxic Gram-negative bacterial strains of the present invention (e.g., the ΔAPI strain) provide improved methods of isolating endotoxin free therapeutic molecules (e.g., lipid IVa). For example, the ΔAPI strain is contemplated to be a host for the production of commercially important therapeutic molecules in an endotoxin-free environment using the well-studied Gram-negative bacteria. Additionally, strains comprising a mutation in gutQ, kdsD, kdsA, kdsB, waaA msbA, yhjD genes, or mutations in any other biosynthetic, processing, or trafficking bacterial genes are contemplated to be hosts for the production of commercially important therapeutic molecules in an endotoxin-free environment using Gram-negative bacteria.

In some embodiments, the viable non-toxic Gram-negative bacteria can be used for production of vaccines or other compositions that stimulate the immune response. For example, a less toxic vaccine against typhoid fever is produced using the Gram-negative bacteria as described herein. Current vaccines for typhoid fever cause side effects due to endotoxins present in the vaccine preparation. It is contemplated that utilizing the viable non-toxic Gram-negative bacteria or portions thereof as described herein where no LPS (e.g., endotoxin) is presented on the outer membrane bypasses side effects caused by endotoxin laced vaccine preparations. The present invention finds utility in any vaccine preparation or other composition where endotoxin contamination is typically found. The viable non-toxic Gram-negative bacteria of the present invention are also contemplated to find utility as live attenuated vaccines due to their LPS deficiency phenotype.

As such, the present invention finds use in developing OM vaccines and other compositions for inducing immune responses that are free of endotoxin contamination that can be administered to subjects for immunization and research purposes. For example, attenuated or OM vaccines can be prepared using procedures as described in US Patent Application 2005/0013831 or U.S. Pat. No. 6,558,677, incorporated herein by reference in their entireties. For example, such a vaccine finds utility in immunizing subjects at risk of acquiring septic shock (e.g., from *E. coli*), such as surgery patients. Further, endotoxin free attenuated or OM vaccines can be developed for immunization against, for example, whooping cough (e.g., *Bordetella* sp.), brucellosis or endotoxic shock (e.g., *Brucella* sp.), pulmonary and respiratory infections (e.g., *Pseudomonas* sp., *Haemophilus* sp., *Moraxella* sp.), cholera (e.g., *Vibrio* sp.), pneumonia (e.g., *Klebsiella* sp., *Haemophilus* sp.), stomach ulcers (e.g., *Helicobacter* sp.), meningitis (e.g., *Neisseria* sp., *Haemophilus* sp.), otitis media (e.g., *Haemophilus* sp., *Moraxella* sp.), dysentery and diarrhea (e.g., *Shigella* sp., *E. coli, Vibrio* sp., *Campylobacter* sp., *Yersenia* sp.), enteric fevers (e.g., *Salmonella* sp.), trachoma and sexually transmitted diseases (e.g., *Chlamydia* sp.), tularemia (e.g., *Franciscella* sp.), and plague (e.g., *Yersinia* sp.).

In some embodiments, the non-toxic viable Gram-negative bacteria as described herein find utility in generating therapeutic antibodies for therapeutic and research applications. For example, in some embodiments subjects are actively immunized using the non-toxic Gram-negative bacteria or portions thereof (e.g., membrane preparations), and antibodies prepared from human hyper-immune sera are then used to passively protect subjects against bacterial infection and sepsis. However, the generation of therapeutic antibodies is more traditionally accomplished in host animals such as, but are not limited to, primates, rabbits, dogs, guinea pigs, mice, rats, sheep, goats, etc. Therapeutic antibodies, for example, are created using the non-toxic viable Gram-negative bacteria as immunogens themselves for creating antibodies in host animals for administration to human subjects. Non-toxic viable Gram-negative bacteria as described herein additionally find utility as hosts for presenting a foreign antigen (e.g., immunogenic peptide or protein) that is used to create therapeutic antibodies in a host animal. For example, the non-toxic viable Gram-negative bacteria, besides being substantially deficient in LPS, can be genetically manipulated (e.g., via established cloning methods known to those skilled in the art) to express non-native proteins and peptides that find use as immunogens for antibody production. Such immunogens include, but are not limited to, peptides for targeting antibodies to cancer cells and other disease causing cells, viral coat proteins for viral cell targeting, and the like.

In some embodiments, the present invention provides non-toxic viable Gram-negative bacteria useful for presenting immunogenic proteins for therapeutic antibody production. An antibody against an immunogenic protein may be any monoclonal or polyclonal antibody, as long as it can recognize the antigenic protein. Antibodies can be produced according to a conventional antibody or antiserum preparation process known to those skilled in the art.

In some embodiments, viable Gram-negative bacteria (e.g., *E. coli*) comprising an outer membrane expressing lipid IVa are used for purposes of pharmaceutical screening (e.g., screening for anti-pyrogenic agents). The ΔAPI mutant strain has a very low permeability barrier, making it particularly susceptible to large, hydrophobic drug molecules that normally cannot penetrate the OM. Whole cell bioassays of compound libraries normally use permeabilizing agents such as toluene, EDTA, cationic peptides, etc. to help identify hits by facilitating penetration of the OM. Once parent lead hits are made, medicinal chemistry can be used to improve the solubility, partitioning, size, etc. to produce an antibiotic. Many potential leads from these screens are missed because the compound cannot gain access to its protein target inside the OM. Using, for example, the ΔAPI mutant strain in such screens alleviates OM permeability problems by lowering the permeability barrier without the need for providing additional reagents. Similarly, such low OM permeability of the ΔAPI is an advantage when transforming, for example, the ΔAPI mutant strain with DNA plasmids during the generation of DNA libraries. High transformation efficiency cells are essential to all recombination DNA technologies, and the ΔAPI strain is a useful host for such applications.

EXAMPLES

Example I

This example describes the ΔAPI mutants TCM15 and KPM22. An auxotrophic ΔAPI mutant with both G-API and L-API deleted, TCM15, was constructed which became dependent on exogenous A5P for growth in accordance with the established $KDO_2$-lipid A dogma for E. coli. TCM15 was incapable of forming colonies on solid media, regardless of the growth media, incubation temperature, or time without including A5P. When cultured in liquid MOPS-minimal media with 0.2% glycerol as a sole carbon source, cell division routinely resumed after a 32-48 hour lag despite the lack of A5P.

The E. coli KPM22 strain was shown to be a non-conditional ΔAPI mutant capable of sustained growth in rich media without an initial lag at 37° C. although there remained no measurable API activity in cellular extracts. As shown in Table 2, the doubling time increased to nearly twice that of the parent wild-type strain in LB media.

TABLE 2

Generation Times in LB media at Various Temperatures

| Strain | 30° C. (min) | 37° C. (min) | 42° C. (min) |
|---|---|---|---|
| BW30270 | 39 | 24 | 22 |
| KPM22 | 55 | 38 | N/A $_a$ |
| KPM25 | 40 | 25 | 23 |

$_a$ After 2-3 generations, growth rate was non-exponential.

After shifting to non-permissive temperatures (42° C.), exponential growth rates were not maintained after 2 to 3 generations. Growth was restored to KPM22 at elevated temperatures by a plasmid encoding kdsD (KPM25), suggesting a defective cell envelope due to the block in KDO synthesis.

To further investigate KPM22, LPS samples were extracted from cells using the phenol-chloroform-petroleum ether (PCP) extraction method (see, e.g., C. Galanos, et al., Eur. J. Biochem. 9, 245 (1969); herein incorporated by reference in its entirety). The saccharide composition of the LPS extract was determined for the inner core sugar constituents [KDO and L-glycero-D-manno-heptose (heptose)] and lipid A [D-glucosamine (GlcN)] (see FIG. 1A). The ratios for both wild-type BW30270 [1 GlcN: 0.9 KDO: 2.2 heptose] and KPM25 [1.0 GlcN: 1.0 KDO: 2.5 heptose] were consistent with the ratio for the predominant LPS species (glycoform I) elaborated by E. coli K-12 [1.0 GlcN: 1.0 KDO: 2.0 heptose] (see, e.g., S. Müller-Loennies, et al., J. Biol. Chem. 278, 34090 (2003); herein incorporated by reference in its entirety). Only traces of KDO or heptose were detected in comparison for KPM22, though GlcN was still present suggesting that the lipid A backbone was intact.

Silver stained SDS-PAGE analysis of LPS samples prepared from proteinase K treated whole-cell lysates detected no bands for KPM22 (see, FIG. 1B; top panel). Blotted membranes were treated with acid to cleave the saccharide core before being probed with the mAb A6 antibody, which recognized the nonglycosylated 1,4'-bisphosphorylated β-1,6-linked GlcN disaccharide backbone of lipid A. A single band from KPM22 that migrated faster than the Re endotoxin standard but at the same level as synthetic lipid IVa was recognized by the antibody (FIG. 1B, middle panel, lanes 6 and 16, respectively). Only LPS samples prepared from KPM22 together with synthetic lipid IVa were recognized by mAb A6 when the acid hydrolysis step was omitted, confirming the native lipid A structure was nonglycosylated (FIG. 1B, bottom panel).

Figure 2:
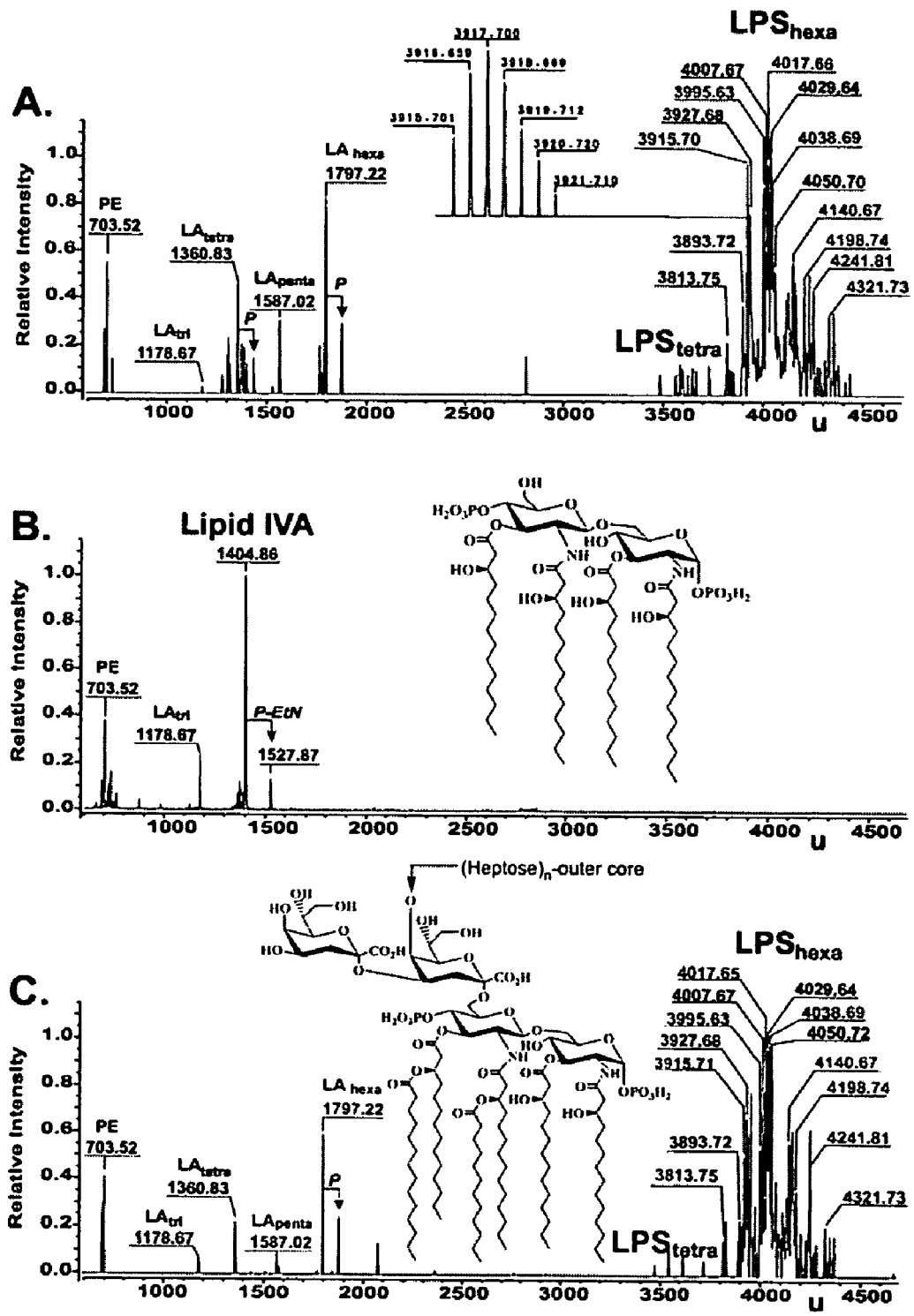
FIG. 2 presents characterization of the LPS precursor in KPM22. Charge deconvoluted electrospray ionization Fourier transform ion cyclotron (ESI FT-ICR) mass spectra in negative ion mode of purified LPS samples. Mass numbers given refer to the monoisotopic masses of the neutral molecules.

The chemotype of the LPS precursor in KPM22 was determined by electrospray ionization Fourier transform ion cyclotron (ESI FT-ICR) mass spectrometry in negative ion mode using purified LPS samples (see, FIG. 2, Table 3).

TABLE 3

ESI FT-ICR MS Peak List

| Obs. Mass $_{a,b}$ | Calc. Mass $_a$ | Chemical Composition $_c$ | Label $_c$ |
|---|---|---|---|
| 703.52 | 703.517 | phospholipid, PE (33:1) (e.g. 1* 16:0 + 1*17:1) | PE |
| 1178.67 | 1178.661 | 2*GlcN, 2*P, 3* (OH)-14:0 | $LA_{tri}$ |
| 1360.83 | 1360.828 | 2*GlcN, 2*P, 3* (OH)-14:0, 1* 12:0 | $LA_{tetra}$ |
| 1404.86 | 1404.854 | 2*GlcN, 2*P, 4* (OH)-14:0 | Lipid IVa |
| 1527.87 | 1527.863 | 2*GlcN, 2*P, 4* (OH)-14:0, 1* P-EtN | |
| 1587.02 | 1587.021 | 2*GlcN, 2*P, 4* (OH)-14:0, 1*12:0 | $LA_{penta}$ |
| 1797.22 | 1797.219 | 2*GlcN, 2*P, 4* (OH)-14:0, 1*12:0, 1* 14:0 | $LA_{hexa}$ |
| 3813.75 | 3813.734 | $LA_{hexa}$ + 1*Gal, 3*Glc, 4*Hep, 2*KDO, 2*P | Glycoform I |
| 3893.72 | 3893.700 | $LA_{hexa}$ + 1*Gal, 3*Glc, 4*Hep, 2*KDO, 3*P | Glycoform I |
| 3915.71 | 3915.699 | $LA_{hexa}$ + 1*Gal, 3*Glc, 4*Hep, 2*KDO, 3*P, +1*Na | Glycoform I |
| 3995.63 | 3995.653 | $LA_{hexa}$ + 1*Gal, 3*Glc, 4*Hep, 2*KDO, 4*P, +1*Na | Glycoform I |
| 4017.66 | 4017.645 | $LA_{hexa}$ + 1*Gal, 3*Glc, 4*Hep, 2*KDO, 4*P, +2*Na | Glycoform I |
| 4038.69 | 4038.697 | $LA_{hexa}$ + 1*Gal, 3*Glc, 4*Hep, 2*KDO, 5*P, 1*P-EtN + 1*Na | Glycoform I |
| 3927.68 | 3927.689 | $LA_{hexa}$ + 1*Gal, 2*Glc, 3*Hep, 1*Rha, 3*KDO, 3*P + 1*Na | Glycoform IV |
| 4007.67 | 4007.655 | $LA_{hexa}$ + 1*Gal, 2*Glc, 3*Hep, 1*Rha, 3*KDO, 4*P + 1*Na | Glycoform IV |
| 4029.64 | 4029.654 | $LA_{hexa}$ + 1*Gal, 2*Glc, 3*Hep, 1*Rha, 3*KDO, 4*P + 2*Na | Glycoform IV |
| 4050.70 | 4050.698 | $LA_{hexa}$ + 1*Gal, 2*Glc, 3*Hep, 1*Rha, 3*KDO, 3P + 1*P-EtN, +1*Na | Glycoform IV |
| 4140.67 | 4140.722 | $LA_{hexa}$ + 1*GlcNAc, 1*Gal, 3*Glc, 4*Hep, 2*KDO, 3*P, +2*Na | Glycoform II |
| 4198.74 | 4198.735 | $LA_{hexa}$ + 1*GlcNAc, 1*Gal, 3*Glc, 4*Hep, 2*KDO, 4*P, +1*Na | Glycoform II |
| 4220.73 | 4220.724 | $LA_{hexa}$ + 1*GlcNAc, 1*Gal, 3*Glc, 4*Hep, 2*KDO, 4*P, +2*Na | Glycoform II |
| 4300.68 | 4300.698 | $LA_{hexa}$ + 1*GlcNAc, 1*Gal, 3*Glc, 4*Hep, 2*KDO, 5*P, +2*Na | Glycoform II |
| 4241.81 | 4241.778 | $LA_{hexa}$ + 1*GlcNAc, 1*Gal, 3*Glc, 4*Hep, 2*KDO, 3*P, 1*P-EtN + 1*Na | Glycoform II |

TABLE 3-continued

ESI FT-ICR MS Peak List

| Obs. Mass $_{a,b}$ | Calc. Mass $_a$ | Chemical Composition $_c$ | Label $_c$ |
|---|---|---|---|
| 4321.73 | 4321.745 | $LA_{hexa}$ + 1*GlcNAc, 1*Gal, 3*Glc, 4*Hep, 2*KDO, 4*P, 1*P-EtN + 1*Na | Glycoform II |
| 4343.74 | 4343.734 | $LA_{hexa}$ + 1*GlcNAc, 1*Gal, 3*Glc, 4*Hep, 2*KDO, 4*P, 1*P-EtN + 2*Na | Glycoform II |

$_a$ Mass numbers given refer to the monoisotopic masses of the neutral molecules which were deduced from the negative ion ESI FT-ICR mass spectra of the LPS fraction after charge deconvolution.
$_b$ Bold type peaks are labeled on FIG. 4 in text.
$_c$ Abbreviations: PE—phosphatidylethanolamine; GlcN—D-glucosamine; P—phosphate; P-EtN—phosphoethanolamine; Gal—D-galactose; Glc—D-glucose; Hep—L-glycero-D-manno-heptose; KDO—2-keto 3-deoxy-D-manno-octulosonate; Rha—rhamnose; GlcNAc—N-acetyl D-glucosamine; $LA_{tri, tetra, penta, hexa}$—acylation state of lipid A.

The spectra of both wild-type BW30270 and KPM25 displayed similar peak patterns and heterogeneity within the characteristic mass range [~3900 to ~4300 u] of the different glycoforms of mature E. coli K-12 LPS core (see, FIGS. 2A,C). One LPS related peak in KPM22 had a molecular mass of 1404.86 u which was consistent with the structure of 1,4'-bisphosphorylated tetraacylated lipid A (lipid IVa, calculated mass 1404.854 u) (see, FIG. 2B).

Lipid IVa is an intermediate in the LPS pathway that serves as the acceptor for the sequential addition of two KDO residues to form $KDO_2$-lipid IVa, wherein the late acyltransferases LpxL and LpxM next transfer the fatty acids laurate and myristate, respectively, to $KDO_2$-lipid IVa forming hexaacylated $KDO_2$-lipid A. Raetz and coworkers have shown that both enzymes from E. coli display an absolute substrate requirement for KDO in the lipid substrate for activity (see, e.g., K. A. Brozek, C. R. Raetz, J. Biol. Chem. 265, 15410 (1990); herein incorporated by reference in its entirety), explaining the lack of secondary acyl chains in lipid A from KPM22.

Figure 3:
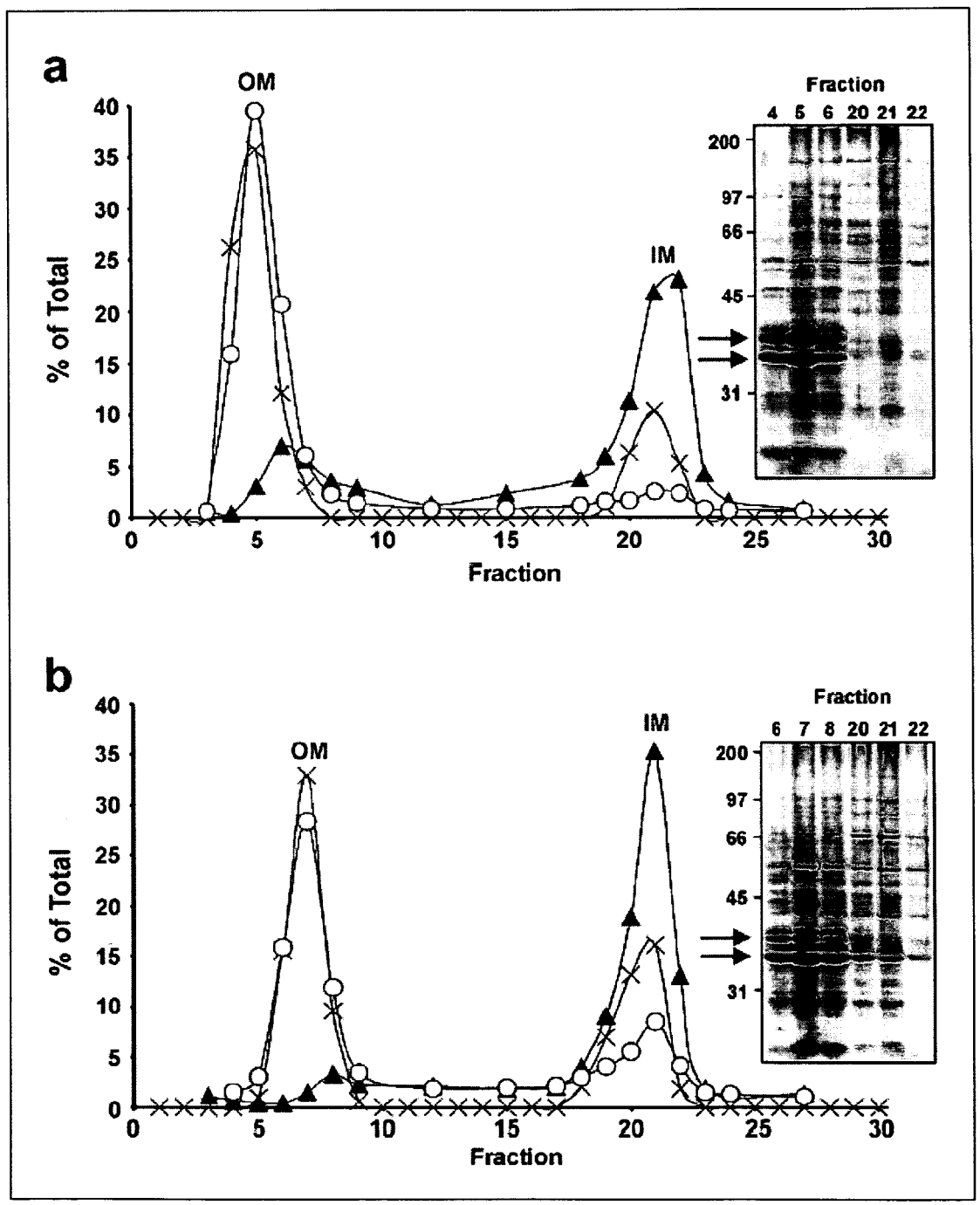
FIG. 3 presents sucrose gradient separation of the inner and outer membranes of wildtype BW30270 (a) and KPM22 (b). Fractions were assayed for total protein content (X), outer membrane phospholipase A (OMPLA) (○), and inner membrane NADH oxidase (▲). SDS-PAGE gels (12%) of protein samples were run under reducing conditions. Molecular mass protein markers (kDa) are listed on the left side of each gel. Arrows indicate the position of OMP proteins (~35 kDa) [Q2].

In order to address the subcellular location of lipid IVA and determine whether it is transported to the OM of KPM22, discontinuous sucrose gradient centrifugation was used to separate the OM from the inner membrane (IM) (see, FIG. 3). Both membranes were well resolved, though the OM for KPM22 did not migrate as far as the wildtype OM, suggesting a decrease in buoyant density. Aside from an increase in the amount of OM porin (OMP) proteins (~35 kDa) remaining localized in the IM at the expense of accumulating in the OM, the overall total protein content and constitution as analyzed by SDS-PAGE was similar. As it has been shown that many OM proteins depend on the molecular chaperone properties of LPS for both their folding and function (see, e.g., H. de Cock, J. Tommassen, Embo J. 15, 5567 (1996); P. V. Bulieris, et al., J. Biol. Chem. 278, 9092 (2003); K. Sen, H. Nikaido, J. Bacteriol. 173, 926 (1991); herein incorporated by reference in their entireties), the decrease in OMPs may reflect a decrease in protein transport rates and/or insertion efficiency into the OM of KPM22. Isolated OM fractions were assayed for the presence of 3-hydroxy myristate (3-OH C14:0), a characteristic LPS/lipid IVA fatty acid marker. The OM of wildtype and KPM22 contained 11.7 and 31.1 µg of 3-OH C14:0 per mg of dried membrane, respectively, suggesting substantial quantities of lipid WA at least equal to the amount of LPS in wildtype are in fact present in the OM of KPM22. Further, ESI FT-ICR mass spectrometry revealed peaks for lipid IVA in both the OM and IM of KPM22, whereas no peaks attributable to lipid WA were detected in either membrane fraction from wildtype. Collectively, this indicates that while lipid IVA is transported to the OM of KPM22, the rate of lipid IVA transport has become uncoupled to its rate of synthesis.

Secondary acyl chains are implicated in maintaining a low degree of fluidity within the OM by increasing the number of acyl chains (see, e.g., H. Nikaido, Microbiol. Mol. Biol. Rev. 67, 593 (2003); herein incorporated by reference in its entirety), a condition required for function. The tight packing of saturated acyl chains induces a network of hydrophobic interactions that that maintains the integrity of the OM outer leaflet through van der Waals forces. Despite containing only four acyl chains and no inner saccharide core, lipid IVa is transported to and is then capable of supporting OM biogenesis in KPM22. The unprecedented nature of a lipid IVa layer in the OM of KPM22 redefines the requisite LPS structure for viability in Enterobacteriaceae.

KDO is normally considered an essential component of a functional LPS layer as only conditional mutants of KDO biosynthetic enzymes in E. coli have been constructed to date (see, e.g., C. J. Belunis, et al., J. Biol. Chem. 270, 27646 (1995); R. C. Goldman, W. E. Kohlbrenner, J. Bacteriol. 163, 256 (1985); P. D. Rick, M. J. Osborn, Proc. Natl. Acad. Sci. U.S.A. 69, 3756 (1972); each herein incorporated by reference in their entireties). This has been attributed to the role of KDO (and arguably in part to other sugars attached distal to KDO) in maintaining a low degree of fluidity within the lipid bilayer (see, e.g., H. Nikaido, Microbiol. Mol. Biol. Rev. 67, 593 (2003); herein incorporated by reference in its entirety). Divalent cations, namely $Mg^{2+}$ and $Ca^{2+}$, are believed to form ionic bridges with the negative charges contributed by both the phosphorylated lipid A backbone and the carboxylate of KDO, minimizing electrostatic repulsion and fostering strong lateral interactions. Further, the location of KDO at the surface of the OM places KDO in close proximity to OM proteins, many of which depend on the molecular chaperone properties of core-containing LPS for both their folding and function (see, e.g., H. de Cock, J. Tommassen, Embo J. 15, 5567 (1996); P. V. Bulieris, et al., J. Biol. Chem. 278, 9092 (2003); K. Sen, H. Nikaido, J. Bacteriol. 173, 926 (1991); herein incorporated by reference in their entireties).

To verify the nonessential nature of KDO in KPM22, genes encoding the first committed step (kdsA) and the last step (waaA) in KDO biosynthesis were disrupted. In contrast to KPM22/KPM25 (FIG. 1B, lanes 8, 9), neither exogenous A5P nor plasmid borne API restored mature LPS synthesis in either KPM31/KPM40 (lanes 12, 15) or KPM34/KPM42 (lanes 11, 14), respectively, consistent with the ability of KPM22 to survive without the entire KDO pathway.

Figure 4:
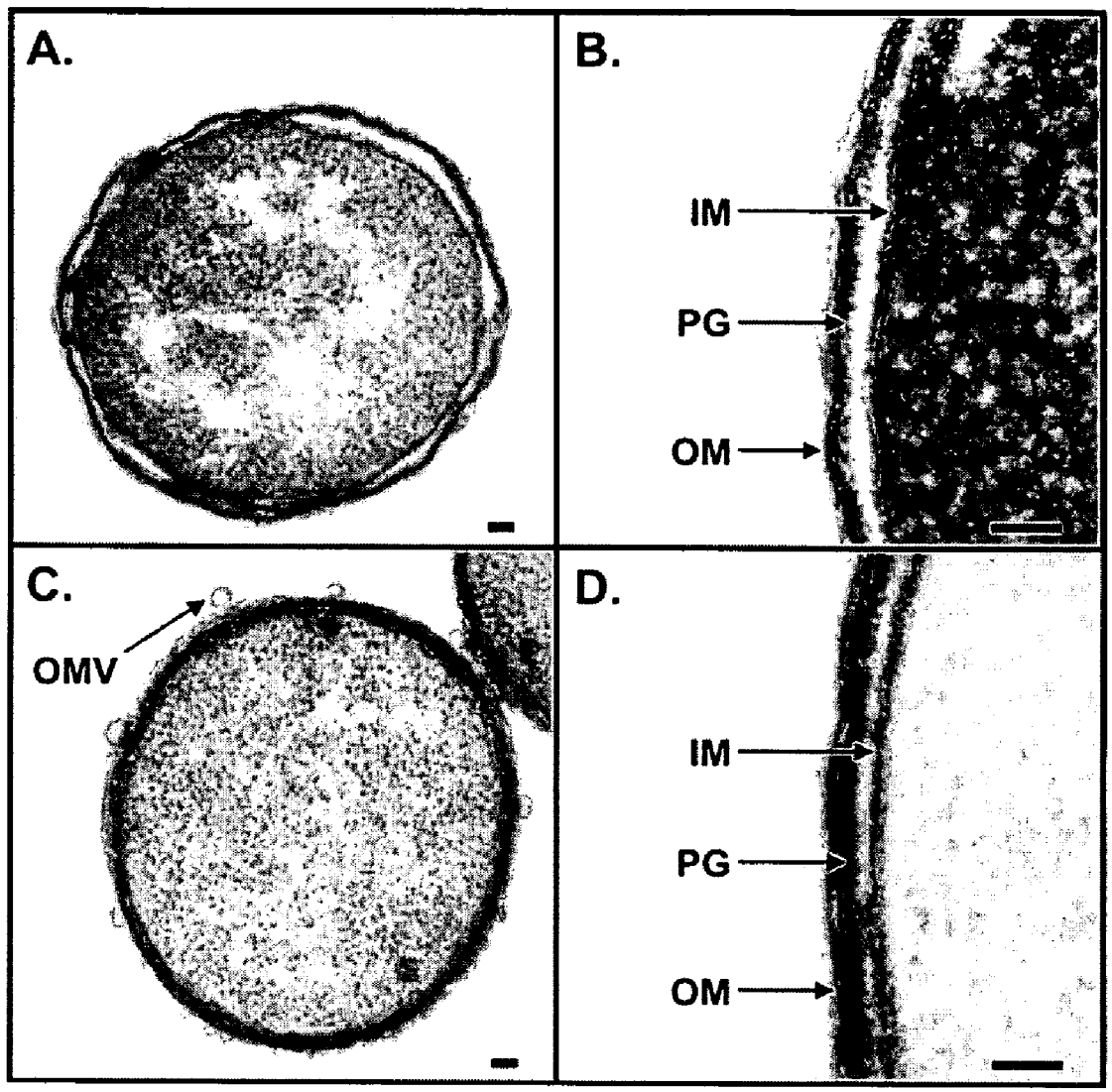
FIG. 4 presents characterization of KPM22. Transmission electron microscopy (TEM) images of wild-type BW30270 (panels A and B) and of KPM22 (panels C and D). Arrows indicate outer membrane vesicles (OMV) at the OM surface of KPM22 (panel C). IM—Inner membrane, OM—Outer membrane, PG—peptidoglycan. Scale bars=50 nm.

The cell morphology of KPM22 was examined by transmission electron microscopy (TEM). Overall, the structure of KPM22 was quite similar to the parent strain (FIG. 4). Obvious division defects were not observed by TEM and cells maintained the normal rod shape. Two clearly distinct membranes were discerned for KPM22 (FIG. 4D), as well as a region between the two membranes representing the periplasm. The periplasmic volume was uniformly compressed in comparison to wild-type. OM instability was suggested by the small membrane vesicles appearing at the surface of KPM22 (FIG. 4C). Outer membrane vesicle (OMV) formation may have been caused by electrostatic repulsion between the 1,4'-GlcN phosphates of neighboring lipid IVa molecules that are not compensated by stabilizing interactions of the saccharide core, increasing the membrane curvature, and resulting in vesicle extrusion from the bacterial surface. Charge repulsion was particularly relevant for KPM22 considering that ESI-MS analysis detected no 4-amino 4-deoxy-L-arabinose and only minimal phosphoethanolamine modifications, both of which served to reduce the amount of net negative charge (see, e.g., C. R. Raetz, C. Whitfield, Annu. Rev. Biochem. 71, 635 (2002); herein incorporated by reference in its entirety).

Figure 5:
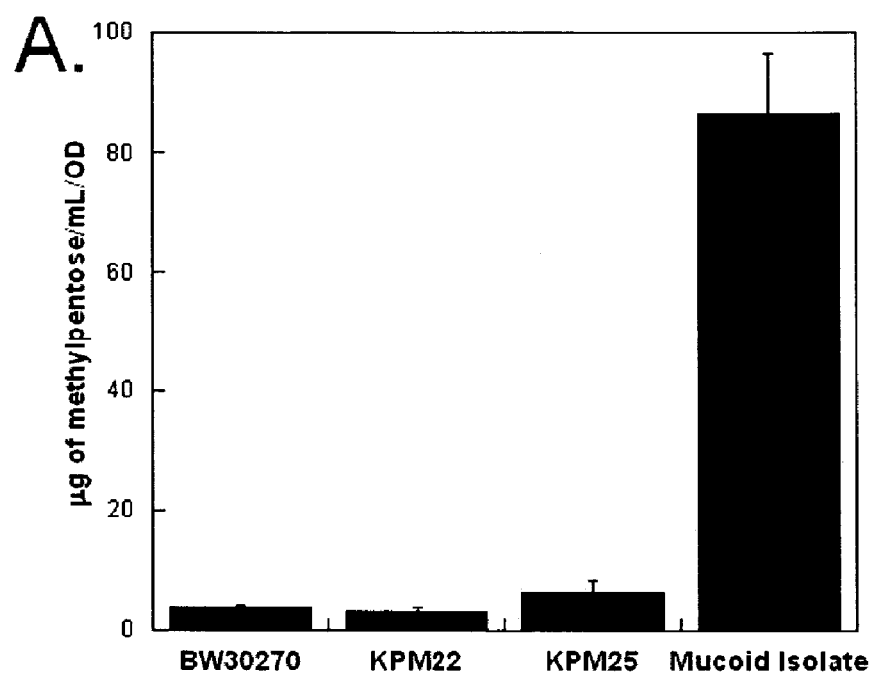
FIG. 5 presents characterization of KPM22.
Figure 5:
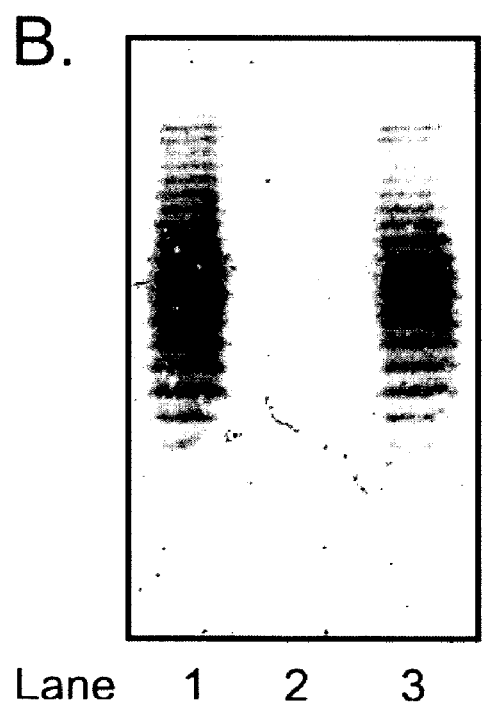
Figure 6:
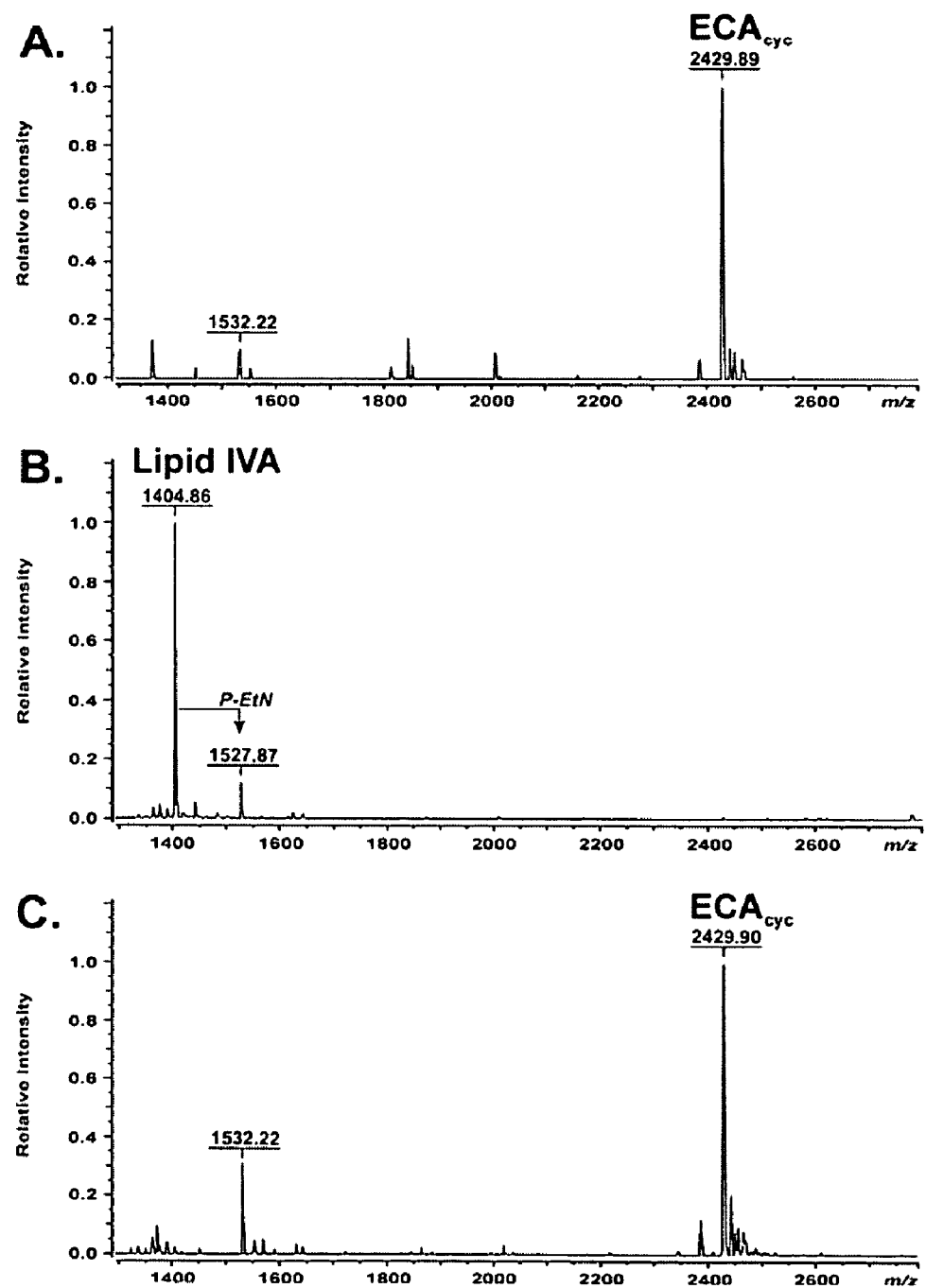
FIG. 6 presents ESI FT-ICR mass spectra of phenol phase extracts. Charge deconvoluted negative ion ESI FT-ICR mass spectra of phenol phase from BW30270 (A), KPM22 (B), and KPM25 (C). LPS was precipitated from crude phenol extracts by the dropwise addition of water. After clarification by centrifugation, the phenol supernatant was dialyzed and treated as described above. Note lipid IVa was not precipitated from the phenol phase by water during this procedure (B). $ECA_{cyc}$—cyclic enterobacterial common antigen (ECA).

Compensatory mechanisms in KPM22 to accommodate the loss in OM integrity due to the extreme LPS truncation invoked stabilization with other OM-bound glycolipids. In an LPS-deficient mutant from *N. meningitidis*, it was reported that capsular polysaccharide synthesis became absolutely necessary for viability (see, e.g., P. van der Ley, L. Steeghs, J. Endotoxin. Res. 9, 124 (2003). *E. coli* K-12 did not synthesize a capsular polysaccharide, but there are two other cell surface polysaccharides in addition to LPS, namely the stress-induced slime exopolysaccharide colanic acid (M-antigen) (see, e.g., A. Markovitz, in Surface carbohydrates of the prokaryotic cell I. W. Sutherland, Ed. (Academic Press, Inc., New York, N.Y., 1977), vol. I, pp. 415-462); herein incorporated by reference in its entirety) and the phosphoglyceride-linked enterobacterial common antigen (ECA) (see, e.g., H. M. Kuhn, et al., FEMS Microbiol. Rev. 4, 195 (1988); herein incorporated by reference in its entirety). There was no difference in the level of nondialyzable methylpentose (FIG. 5A), a constituent carbohydrate marker of colanic acid (see, e.g., S. Gottesman, et al., J. Bacteriol. 162, 1111 (1985); herein incorporated by reference in its entirety). Immunoblot analysis of cell lysates revealed that the amount of glycerophosphatidyl-bound ECA was actually diminished in KPM22 (FIG. 5B), consistent with the disappearance of cyclic-ECA containing four trisaccharide repeating units (2429.89 u) from the KPM22 spectrum of the phenol extract (FIG. 6). Thus, in addition to lipid IVa, the OM of KPM22 contained trace levels of ECA and comparably low wild-type levels of colanic acid. Collectively, the KPM22 envelope represents the most minimal OM glycolipid content reported in *E. coli* capable of sustaining viability.

A main function of the LPS layer is to act as a permeability barrier towards the diffusion of both large, hydrophobic molecules and defensins (polycationic peptides) into the cell as well as to retain the contents of the periplasmic compartment. The strong lateral interactions between adjacent LPS molecules within the OM makes the LPS layer particularly well suited for such a function, in addition to providing a measure of nonspecific defense against host responses. Selective permeation of small hydrophilic molecules, nutrients, and antibiotics is achieved through outer membrane porin (OMP) protein channels. A panel of antibiotics and detergents were screened against KPM22 to gauge the effectiveness of lipid IVa as a permeability barrier (see Table 4).

TABLE 4

Permeability Barrier Properties of KPM22
Minimum Inhibitory Concentration (μg/mL)

| Compound | MW (g mol$^{-1}$) | XlogP | BW30270 (μg mL$^{-1}$) | KPM22 (μg mL$^{-1}$) | Fold Difference |
|---|---|---|---|---|---|
| Rifampin | 822.9 | 3.72 | 16 | 0.03 | 512 |
| Fusidic Acid | 516.7 | 3.7 | 512 | 2 | 256 |
| Novobiocin | 612.6 | 2.74 | 256 | 1 | 256 |
| Erythromycin | 733.9 | 1.98 | 128 | 1 | 128 |
| Bacitracin [a] | 1422.7 | −1.03 | 4096 | 512 | 8 |
| Vancomycin | 1449.3 | −0.47 | 256 | 32 | 8 |
| Kanamycin | | | 16 | 1 | 16 |
| Chloramphenicol | 323.1 | 1.476 | 8 | 2 | 4 |
| Ampicillin | 349.4 | 0.255 | 4 | 2 | 2 |
| Cephaloridine | 416.5 | 1.73 | 4 | 4 | 1 |
| Sodium dodecyl sulfate (SDS) | | | >32000 | 8 | >4000 |
| Bile Salts [b] | | | 16000 | 128 | 125 |
| Polymyxin E [c] | | | 0.25 | 0.06 | 4 |

[a] 74,000 units/g.
[b] Mixture of sodium cholate and deoxycholate.
[c] Colistin; 20,261 units/mg KPM22 was super susceptible to a number of large, hydrophobic antibiotics that typically have reasonable efficacy against only Gram-positive bacteria. Normally denied access to their sites of action by the OM, these compounds accessed intracellular targets in KPM22. Access to the membrane surface was not impeded by the saccharide core, further facilitating the partitioning and subsequent permeation through the compromised lipid bilayer. However, the minimum inhibitory concentration (MIC) of small (<600 Da), relatively hydrophilic compounds that gain passage across the OM primarily through OMPs were at best only modestly decreased. A notable exception was the positively charged aminoglycoside kanamycin. It has been suggested that aminoglycosides gain entry primarily through a self-promoted mechanism of uptake involving initial charge pairing interactions with LPS independent of OMPs (see, e.g., R. E. Hancock, et al., Antimicrob. Agents. Chemother. 35, 1309 (1991); herein incorporated by reference in its entirety). KPM22 was particularly sensitive to detergents, with over a 4000-fold decrease in the MIC for sodium dodecyl sulfate. Since the concentration of bile salts (cholesterol metabolites) in the human intestinal tract ranges from 4 to 16 mM (~1650-6650 μg/mL) (see, e.g., B. Borgstrom, Acta Med. Scand. 196, 1 (1974); herein incorporated by reference in its entirety), the compromised OM of KPM22 would no longer be suited to protect the cell from its host environment. Surprisingly, the MIC of polymyxin E (colistin), a cationic peptide with a detergent-like mechanism of action, was depressed only ~4 fold in KPM22. Accumulation of polymyxins at the membrane surface to the critical aggregate concentration is pertinent to forming micellar lesions within the lamellar bilayer, that subsequently act as channels for self-promoted transport through the OM (see, e.g., A. Wiese et al., J. Membr. Biol. 162, 127 (1998); herein incorporated by reference in its entirety). Lipid IVa has a decreased charge to surface area ratio in comparison to LPS, highlighting the role of the negatively charged inner core residues in polymyxin binding. As the antibiotics chosen have various mechanisms of action, the changes in MICs among hydrophobic compounds is likely a consequence of changes in permeability as opposed to a reflection of general fitness or drug efflux mechanisms. The permeability properties of KPM22 demonstrate the potential of KDO biosynthesis inhibition as a means to broaden the spectrum of activity of antibiotics that already exist by lowering the intrinsic resistance of the OM barrier.

Figure 7:
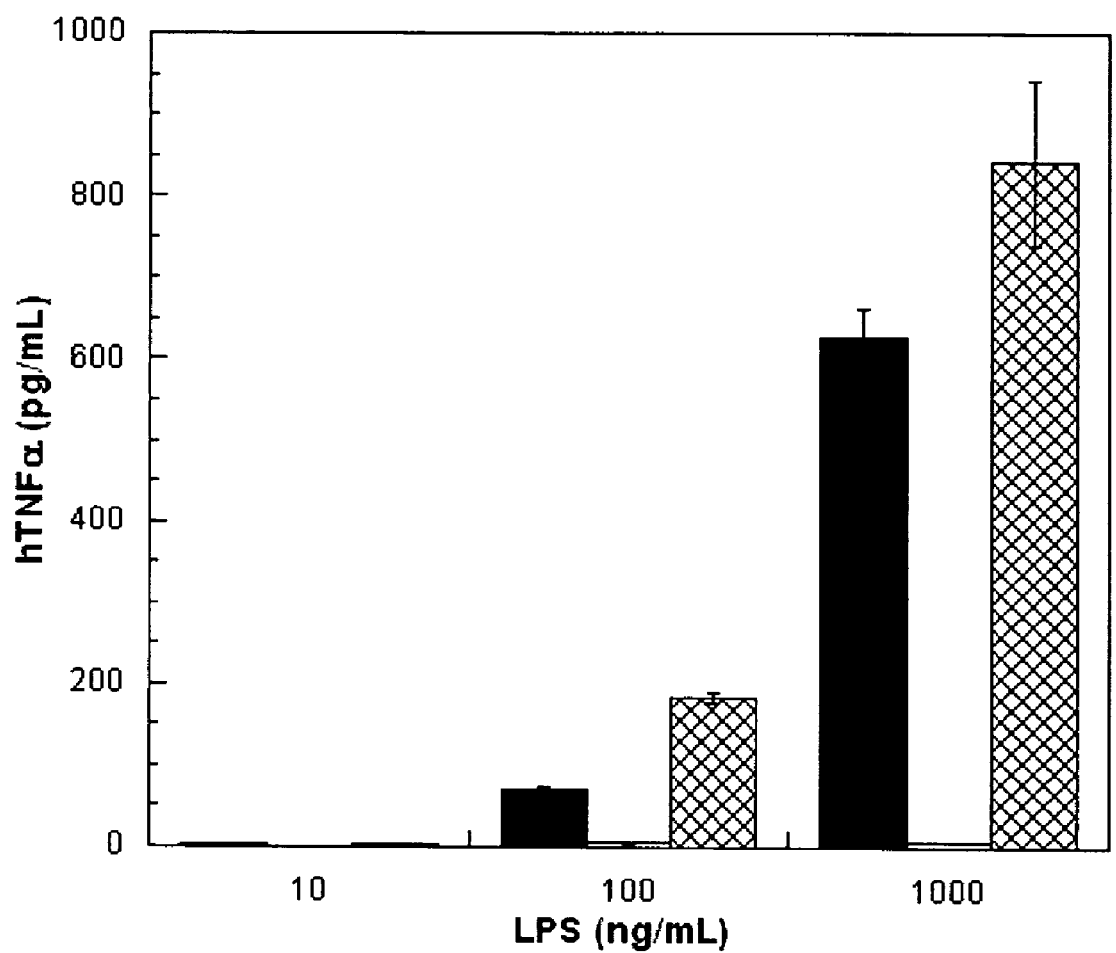
FIG. 7 presents hTNFα cytokine inducing capabilities of LPS preparations. Human mononuclear cells (MNC) were challenged with various concentrations of LPS preparations isolated as described above. hTNFα release was quantitated using an ELISA based assay. Data points were collected in duplicate. (Shaded bars—BW30270, Empty bars—KPM22, Hatched bars—KPM25).

Bacterial endotoxins are potent proinflammatory molecules that elicit an innate immune response in humans even when present in only trace amounts (see, e.g., E. S. Van Amersfoort, et al., Clin. Microbiol. Rev. 16, 379 (2003); herein incorporated by reference in its entirety). Gram-negative bacterial induced septic shock results from an imbalanced, dysregulated immune response. In part, this pathophysiological cascade is triggered by the activation of macrophages by LPS, which in turn secrete an array of inflammatory mediators. One of the first cytokines released by macrophages is the pleiotropic cytokine TNF-α (tumor necrosis factor). The endotoxic potential of LPS preparations were measured using an ELISA based assay for hTNF-α secretion from stimulated human mononuclear cells (FIG. 7). Preparations from KPM22 were endotoxically inactive at concentrations up to 1 μg/mL, consistent with earlier studies using chromatographically purified lipid IVa (see, e.g., D. T. Golenbock, et al., J. Biol. Chem. 266, 19490 (1991); herein incorporated by reference in its entirety). In E. coli and related bacteria, KDO inhibition not only increased the susceptibility of the bacteria to both host responses and antibiotics, but also has the potential to decrease the risk of sepsis by lowering the endotoxin burden.

The inner membrane ABC (ATP binding cassette) transporter that flips LPS from the cytoplasm to the periplasmic face of the IM is highly selective for hexaacylated LPS/lipid A substrates in vitro (see, e.g., Zhou Zhou, Z., et al., J. Biol. Chem. 273, 12466-12475 (1998); Doerrler, W. T., et al., J. Biol. Chem. 277, 36697-36705 (2002); each herein incorporated by reference in their entireties). MsbA was originally identified as a multicopy suppressor of LpxL (HtrB) temperature sensitive phenotypes (see, e.g., Polissi, A., and Georgopoulos, C. Mol. Microbiol. 20, 1221-1233 (1998); herein incorporated by reference in its entirety). Complementation of the auxotrophic TCM15 strain with a cosmid library of KPM22 genomic DNA revealed that MsbA was a multicopy suppressor of the ΔKdo phenotype. Seventeen separate cosmid clones were isolated containing the msbA locus. A cosmid subclone (pMMW52), containing a 3.5 kb insert with only an intact wildtype msbA sequence identical to the wildtype, was able to directly rescue TCM15 without the need to develop the presumed suppressor mutation(s), as indicated by loss of A5P auxotrophy and restoration of colony-forming ability on solid agar (Table 5). The growth rate of TCM15 (pMMW52) is similar to KPM22 (Tables 2 and 5). These results indicate that while lipid IVA is a poor substrate in vitro (see, Doerrler, W. T., and Raetz, C. R., J. Biol. Chem. 277, 36697-36705 (2002); herein incorporated by reference in its entirety), lipid IVa becomes a substrate for MsbA in vivo when present in high concentrations by simple mass action.

TABLE 5

Multicopy suppression of TCM15 auxotrophy by MsbA

| Strain | Colony forming units (cfu) mL$^{-1a}$ | | Growth in liquid LB media$^b$ | |
|---|---|---|---|---|
| | LB Only | LB + A5P/G6P$^{c,d}$ | LB$^d$ | LB + A5P/G6P$^{c,d}$ |
| TCM15 | 0 | $8.7 \times 10^7$ | | +++ (23) |
| TCM15 (pMBL19)$^e$ | 0 | $2.1 \times 10^6$ | | +++ (22) |
| TCM15 (pMMW52)$^f$ | $4.4 \times 10^3$ | $3.1 \times 10^5$ | ++ (33) | +++ (23) |

$^a$Cfu values correspond to either direct plating (TCM15) or post-electrotransformation;
$^b$Where measurable, generation times (min) at 37° C. are listed in parentheses;
$^c$15 μM A5P, 10 μM G6P.
$^d$Amp (100 μg mL − 1) was included for strains carrying plasmid;
$^e$Cloning vector;
$^f$Subclone containing msbA.

Example II

This example describes the bacterial strains, plasmids, and primers used in the studies involving KPM22 and TCM15. The bacterial strains, plasmids, and primers used in the studies involving KPM22 and TCM15 are listed in Table 6.

TABLE 6

Bacterial Strains, Plasmids, and Primers

| Strain/ Plasmid/ Primer | Description $^a$ | Source or Reference |
|---|---|---|
| BW30270 | E. coli K-12 MG1655; rph$^+$ fnr$^+$ | E. coli Genetic Stock Center (CGSC#7925) |
| SL3749 | S. enterica sv. Typhimurium (rfaL446, Ra chemotype of LPS) | Salmonella Genetic Stock Center (SGSC#228) |
| SL3750 | S. enterica sv. Typhimurium (rfaJ417, Rb2 chemotype of LPS) | Salmonella Genetic Stock Center (SGSC#229) |
| SL3748 | S. enterica sv. Typhimurium (rfaI432, Rb3 chemotype of LPS) | Salmonella Genetic Stock Center (SGSC#227) |
| SL3769 | S. enterica sv. Typhimurium (rfaG471, Rd1 chemotype of LPS) | Salmonella Genetic Stock Center (SGSC#231) |
| SL1102 | S. enterica sv. Typhimurium (rfaE543, Re chemotype of LPS) | Salmonella Genetic Stock Center (SGSC#258) |

TABLE 6-continued

Bacterial Strains, Plasmids, and Primers

| Strain/Plasmid/Primer | Description[a] | Source or Reference |
|---|---|---|
| TCM15 | BW30270(ΔgutQ ΔkdsD); A5P auxotroph | T. C. Meredith and R. W. Woodard, J. Bacteriol., in press, (2005); herein incorporated by reference in its entirety) |
| KPM22 | TCM15 MOPS minimal media derivative | Experiments conducted during the course of the present invention |
| KPM25 | KPM22 with pT7kdsD | Experiments conducted during the course of the present invention |
| KPM31 | KPM22(ΔkdsA) | Experiments conducted during the course of the present invention |
| KPM34 | KPM31 with pT7kdsD | Experiments conducted during the course of the present invention |
| KPM40 | KPM22(ΔwaaA) | Experiments conducted during the course of the present invention |
| KPM42 | KPM40 with pT7kdsD | Experiments conducted during the course of the present invention |
| PT7kdsD | pT7-7 with E. coli K-12 kdsD; Amp[R] | T. C Meredith and R. W. Woodard, J. Biol. Chem., 278, 32771 (2003); herein incorporated by reference in its entirety) |
| P1 | GCTGCATTAATTAATCGACATTTT ACTCAAGATTAAGGCGATCCTGT GTAGGCTGGAGCTGCTTC (SEQ ID NO: 9) | Invitrogen |
| P2 | GTCTTAACGCAGAACGCTAATACT TTATTTTTCAAGCAAAAAAGAATT CCGGGGATCCGTCGACC (SEQ ID NO: 10) | Invitrogen |
| P3 | ACAGCTAAATACATAGAATCCCC AGCACATCCATAAGTCAGCTATTT ACTGTGTAGGCTGGAGCTGCTTC (SEQ ID NO: 11) | MWG Biotech |
| P4 | TAATGGGATCGAAAGTACCCGGA TAAATCGCCCGTTTTTGCATAACA ACCCATATGAATATCCTCCTTAG (SEQ ID NO: 12) | MWG Biotech |

[a] Homology regions are underlined.

All strains were grown in standard Luria-Bertani media (10 g Tryptone, 5 g Yeast Extract, 10 g NaCl) or MOPS-minimal media (see, e.g., F. C. Neidhardt, P. L. Bloch, D. F. Smith, J. Bacteriol. 119, 736 (1974); herein incorporated by reference in its entirety) with 0.2% glycerol as the sole carbon source. E. coli strain KPM22 was used as the host for chromosomal kdsA and waaA gene disruptions using the phage λ Red recombinase system according to the procedure of Datsenko and Wanner (see, e.g., K. A. Datsenko, B. L. Wanner, Proc. Natl. Acad. Sci. U.S.A. 97, 6640 (2000); herein incorporated by reference in its entirety). Kanamycin and ampicillin were used at 15 μg/mL and 100 μg/mL, respectively. Primer pairs P1/P2 with pKD13(kan) or P3/P4 with pKD4(kan) as templates were used to construct insert cassettes for KPM31 and KPM40, respectively. Antibiotic resistance markers were excised using the FLP recombinase system as described (see, e.g., K. A. Datsenko, B. L. Wanner, Proc. Natl. Acad. Sci. U.S.A. 97, 6640 (2000); herein incorporated by reference in its entirety), except all plasmids were cured at 37° C.

Example III

This example describes the growth of KPM22. Growth of KPM22 involved exponentially dividing cultures of TCM15 in MOPS-minimal media supplemented with 10 μM D-glucose 6-phosphate and 15 μM D-arabinose 5-phosphate at 37° C. were diluted (1:200 v/v) into the same media lacking the sugar phosphate supplements. After an initial lag lasting from 24-32 hours, growth resumed and cultures were colony purified on LB agar plates.

Example IV

This example describes the growth rate determinations for experiments involving KPM22. Overnight cultures were grown at 30° C. and used to inoculate fresh prewarmed LB media (30° C., 37° C., or 42° C.) to an $OD_{600\,nm}$ equal to 0.05-0.1. Growth was monitored by measuring the change in $OD_{600\,nm}$ and cultures were diluted as the OD approached ~0.7 to maintain exponential growth. Doubling times are listed in Table 7.

TABLE 7

Generation Times in LB media at Various Temperatures

| Strain | 30° C. (min) | 37° C. (min) | 42° C. (min) |
|---|---|---|---|
| BW30270 | 39 | 24 | 22 |
| KPM22 | 55 | 38 | N/A $_a$ |
| KPM25 | 40 | 25 | 23 |

$_a$ After 2-3 generations, growth rate was non-exponential.

Example V

This example describes LPS purification for experiments involving KPM22 and TCM15. Samples were routinely prepared by growing 500 mL of each strain in LB media at 37° C. with constant aeration at 250 rpm. Cells from stationary phase cultures were collected by centrifugation (10 min, 8000×g, 4° C.), washed in distilled water, and recentrifuged. The biomass was dehydrated by treatment with ethanol (95%), acetone, and diethyl ether as described previously (see, e.g., U. Zahringer et al., J. Biol. Chem. 279, 21046 (2004); herein incorporated by reference in its entirety). Isolation of LPS was performed by extraction of the dried cells according to the phenol-chloroform-petroleum ether procedure (see, e.g., C. Galanos, O. Lüderitz, O. Westphal, Eu.r J. Biochem. 9, 245 (1969); herein incorporated by reference in its entirety). Aliquots of the crude phenol extract to be analyzed for carbohydrate composition (FIG. 1A) were extensively dialyzed against distilled water (MWCO=1000 Da), and collected by lyophilization. LPS samples for mass spectrometry analysis and measurement of human TNFα cytokine release were purified from the crude phenol phase by precipitation via the dropwise addition of water. A flocculent precipitate only formed for BW30270 and KPM25, which was collected by centrifugation and successively washed with 80% phenol and then acetone. Precipitates were dissolved in water, and dialyzed separately from their respective phenol phase mother liquor. After lyophilization, samples were resuspended in buffer (20 mM Tris-HCl, pH=7.5, 10 mM NaCl, 10 mM $MgCl_2$), treated with DNase I (20 μg/mL) and RNase A (20 μg/mL) for 8 hours at 37° C., followed by proteinase K (100 μg/mL) for 16 hours. LPS samples were collected by ultracentrifugation (SW 41 Ti swingbucket rotor, 200,000×g, 2 hours, 15° C.), washed three times with distilled water, and extensively dialyzed against water before lyophilization. Representative LPS purification yields are listed in Table 8.

TABLE 8

LPS Purification Summary

| Strain | Final $OD_{600nm}$ | Wet Cell Mass (g) | Dry Cell Mass (g) | Ppt.$_a$ Observed | Phenol Soluble (mg) | LPS ppt. (mg) | Purified Yield $_b$ (mg) | % Yield $_c$ |
|---|---|---|---|---|---|---|---|---|
| BW30270 | 5.27 | 2.50 | 0.56 | + | 7.0 | 13.5 | 12.1 | 2.1 |
| KPM22 | 3.61 | 1.88 | 0.43 | − | 13.3 | N/A | 7.2 | 1.7 |
| KPM25 | 5.75 | 2.58 | 0.65 | + | 9.1 | 15.7 | 13.0 | 2.0 |

$_a$Ppt.—precipitate.
$_b$After DNase I/RNase A/proteinase K treatment.
$_c$Based on dry cell mass.

Example VI

This example describes the carbohydrate composition analysis for experiments involving KPM22 and TCM15. The D-glucosamine (GlcN), 2-keto 3-deoxy-D-manno-octulosonate (KDO), and L-glycero-D-manno-heptose (heptose) content of LPS samples from the crude phenol extract were determined using colorimetric chemical assays. GlcN content was determined by hydrolysis of LPS samples (~1 mg) in 500 μL of 4 M HCl at 100° C. for 18 hours. Liberated GlcN was quantitated using the acetyl amino sugar assay (see, e.g., J. L. Strominger, J. T. Park, R. E. Thompson, J. Biol. Chem. 234, 3263 (1959); herein incorporated by reference in its entirety). KDO content was measured using the LPS-adapted thiobarbituric acid assay (see, e.g., Y. D. Karkhanis, J. Y. Zeltner, J. J. Jackson, D. J. Carlo, Anal. Biochem. 85, 595 (1978); herein incorporated by reference in its entirety), while the amount of heptose was estimated using the modified cysteine-sulfuric acid assay (see, e.g., M. J. Osborn, Proc. Natl. Acad. Sci. U.S.A. 50, 499 (1963); herein incorporated by reference in its entirety).

Example VII

This example describes SDS-PAGE Electrophoresis and Lipid A/ECA Immunoblots for experiments involving KPM22 and TCM15. The LPS profiles of whole-cell lysates were analyzed by SDS-PAGE according to the method of Hitchcock and Brown (see, e.g., P. J. Hitchcock, T. M. Brown, J. Bacteriol. 154, 269 (1983); herein incorporated by reference in its entirety). Briefly, colonies of each sample were scraped from LB agar plates and suspended to equal turbidities in Dulbecco phosphate-buffered saline. Washed cell pellets were collected by centrifugation, lysis buffer (50 μl 62.5 mM Tris-HCl, pH 6.8, 2% SDS, 5% 2-mercaptoethanol, 10% glycerol, 0.002% bromphenolblue) was added, and samples were heated in a boiling water bath for 10 minutes. Proteinase K (25 μg, 10 μl of 2.5 mg/ml) was added to each whole cell lysate and incubated for 1 hour at 56° C. Identical volumes were loaded onto 13% SDS-PAGE gels and then run at constant current (15 mA). Gels were silver stained for LPS analysis (see, e.g., P. J. Hitchcock, T. M. Brown, J. Bacteriol. 154, 269 (1983); herein incorporated by reference in its entirety), or were electrotransferred at constant voltage (26 V) from gels to polyvinylidene difluoride membranes using Tris-glycine buffer (20 mM Tris, 150 mM glycine, pH 8.3, 20% methanol) as described (see, e.g., H. Towbin, T. Staehelin, J. Gordon, Proc. Natl. Acad. Sci. U.S.A. 76, 4350 (1979); herein incorporated by reference in its entirety). Prior to incubation of the blots with mAb A6, which recognizes the nonglycosylated 1,4'-bisphosphorylated β1,6-linked GlcN disaccharide backbone of lipid A (see, e.g., L. Brade, O. Hoist, H. Brade, Infect. Immun. 61, 4514 (1993); herein incorporated by reference in its entirety), the membranes were boiled for 1 hour in 1% acetic acid to cleave the α 2,6-KDO-GlcN linkage before being developed by the usual immuno-procedure (see, e.g., R. Pantophlet, L. Brade, H. Brade, J. Endotoxin Res. 4, 89 (1997); herein incorporated by reference in its entirety). Authentic synthetic lipid IVa (compound 406) was used as a standard (see, e.g., M. Imoto et al., Bull. Chem. Soc. Japan 60, 2197 (1987); herein incorporated by reference in its entirety). Enterobacterial common antigen (ECA) immunoblot was probed using mAb 898 (see, e.g., H. Peters et al., Infect. Immun. 50, 459 (1985); herein incorporated by reference in its entirety). Immunoblots were incubated with alkaline phosphatase-conjugated goat anti-mouse IgG (H+L) and developed in the presence of nitroblue tetrazolium and 5-bromo-4-chloro-3-indolylphosphate substrate.

Example VIII

This example describes Electrospray Ionization Fourier Transform Ion Cyclotron Mass Spectrometry (ESI FT-ICR MS) used in experiments conducted during the course of the present invention. ESI FT-ICR MS was performed in the negative ion mode using an APEX II-Instrument (Bruker Daltonics, Billerica, USA) equipped with a 7 Tesla actively shielded magnet and an Apollo ion source. Mass spectra were acquired using standard experimental sequences as provided by the manufacturer. Samples were dissolved at a concentration of ~10 ng/μl in a 50:50:0.001 (v/v/v) mixture of 2-propanol, water, and triethylamine and sprayed at a flow rate of 2 μl/min. Capillary entrance voltage was set to 3.8 kV, and dry gas temperature to 150° C. The spectra were charge deconvoluted and mass numbers given refer to neutral monoisotopic masses. Peak assignments were interpreted on the basis of the previously published detailed structural analysis of LPS from E. coli K-12 strain W3100 (see, e.g., S. Müller-Loennies, B. Lindner, H. Brade, J. Biol. Chem. 278, 34090 (2003); herein incorporated by reference in its entirety). Only the most abundant ions are summarized in Table 9 as there were some molecular species with overlapping isotopic peaks that could not be identified unequivocally.

TABLE 9

ESI FT-ICR MS Peak List

| Obs. Mass $_{a,b}$ | Calc. Mass $_a$ | Chemical Composition $_c$ | Label $_c$ |
|---|---|---|---|
| 703.52 | 703.517 | phospholipid, PE (33:1) (e.g. 1* 16:0 + 1*17:1) | PE |
| 1178.67 | 1178.661 | 2*GlcN, 2*P, 3* (OH)-14:0 | $LA_{tri}$ |
| 1360.83 | 1360.828 | 2*GlcN, 2*P, 3* (OH)-14:0, 1* 12:0 | $LA_{tetra}$ |
| 1404.86 | 1404.854 | 2*GlcN, 2*P, 4* (OH)-14:0 | Lipid IVa |
| 1527.87 | 1527.863 | 2*GlcN, 2*P, 4* (OH)-14:0, 1* P-EtN | |
| 1587.02 | 1587.021 | 2*GlcN, 2*P, 4* (OH)-14:0, 1*12:0 | $LA_{penta}$ |
| 1797.22 | 1797.219 | 2*GlcN, 2*P, 4* (OH)-14:0, 1*12:0, 1* 14:0 | $LA_{hexa}$ |
| 3813.75 | 3813.734 | $LA_{hexa}$ + 1*Gal, 3*Glc, 4*Hep, 2*KDO, 2*P | Glycoform I |
| 3893.72 | 3893.700 | $LA_{hexa}$ + 1*Gal, 3*Glc, 4*Hep, 2*KDO, 3*P | Glycoform I |
| 3915.71 | 3915.699 | $LA_{hexa}$ + 1*Gal, 3*Glc, 4*Hep, 2*KDO, 3*P, +1*Na | Glycoform I |
| 3995.63 | 3995.653 | $LA_{hexa}$ + 1*Gal, 3*Glc, 4*Hep, 2*KDO, 4*P, +1*Na | Glycoform I |
| 4017.66 | 4017.645 | $LA_{hexa}$ + 1*Gal, 3*Glc, 4*Hep, 2*KDO, 4*P, +2*Na | Glycoform I |
| 4038.69 | 4038.697 | $LA_{hexa}$ + 1*Gal, 3*Glc, 4*Hep, 2*KDO, 5*P, 1*P-EtN + 1*Na | Glycoform I |
| 3927.68 | 3927.689 | $LA_{hexa}$ + 1*Gal, 2*Glc, 3*Hep, 1*Rha, 3*KDO, 3*P + 1*Na | Glycoform IV |
| 4007.67 | 4007.655 | $LA_{hexa}$ + 1*Gal, 2*Glc, 3*Hep, 1*Rha, 3*KDO, 4*P + 1*Na | Glycoform IV |
| 4029.64 | 4029.654 | $LA_{hexa}$ + 1*Gal, 2*Glc, 3*Hep, 1*Rha, 3*KDO, 4*P + 2*Na | Glycoform IV |
| 4050.70 | 4050.698 | $LA_{hexa}$ + 1*Gal, 2*Glc, 3*Hep, 1*Rha, 3*KDO, 3P + 1*P-EtN, +1*Na | Glycoform IV |
| 4140.67 | 4140.722 | $LA_{hexa}$ + 1*GlcNAc, 1*Gal, 4*Hep, 2*KDO, 4*P, +2*Na | Glycoform II |
| 4198.74 | 4198.735 | $LA_{hexa}$ + 1*GlcNAc, 1*Gal, 3*Glc, 4*Hep, 2*KDO, 4*P, +1*Na | Glycoform II |
| 4220.73 | 4220.724 | $LA_{hexa}$ + 1*GlcNAc, 1*Gal, 3*Glc, 4*Hep, 2*KDO, 4*P, +2*Na | Glycoform II |
| 4300.68 | 4300.698 | $LA_{hexa}$ + 1*GlcNAc, 1*Gal, 3*Glc, 4*Hep, 2*KDO, 5*P, +2*Na | Glycoform II |
| 4241.81 | 4241.778 | $LA_{hexa}$ + 1*GlcNAc, 1*Gal, 3*Glc, 4*Hep, 2*KDO, 3*P, 1*P-EtN + 1*Na | Glycoform II |
| 4321.73 | 4321.745 | $LA_{hexa}$ + 1*GlcNAc, 1*Gal, 3*Glc, 4*Hep, 2*KDO, 4*P, 1*P-EtN + 1*Na | Glycoform II |
| 4343.74 | 4343.734 | $LA_{hexa}$ + 1*GlcNAc, 1*Gal, 3*Glc, 4*Hep, 2*KDO, 4*P, 1*P-EtN + 2*Na | Glycoform II |

$_a$ Mass numbers given refer to the monoisotopic masses of the neutral molecules which were deduced from the negative ion ESI FT-ICR mass spectra of the LPS fraction after charge deconvolution.
$_b$ Bold type peaks are labeled on FIG. 4 in text.
$_c$ Abbreviations: PE—phosphatidylethanolamine; GlcN—D-glucosamine; P—phosphate; P-EtN—phosphoethanolamine; Gal—D-galactose; Glc—D-glucose; Hep—L-glycero-D-manno-heptose; KDO—2-keto 3-deoxy-D-manno-octulosonate; Rha—rhamnose; GlcNAc—N-acetyl D-glucosamine; $LA_{tri, tetra, penta, hexa}$—acylation state of lipid A.

Example IX

This example describes the quantitation of colonic acid in experiments involving KPM22 and TCM15. Colanic acid was estimated by a modification of the method reported by Kang and Markovitz (see, e.g., S. Kang, A. Markovitz, J. Bacteriol. 93, 584 (1967); herein incorporated by reference in its entirety). Colonies from LB agar plates were scraped and resuspended in 10 mL of distilled water to identical turbidities ($OD_{600nm}$), immersed in a boiling water bath for 15 minutes to release extracellular polysaccharides, and clarified by centrifugation (10 min, 8000×g). The supernatant was assayed for methylpentose (L-fucose), a constituent of colanic acid, by a specific colorimetric reaction using authentic L-fucose as standard (see, e.g., Z. Dische, L. B. Shettles, J. Biol. Chem. 175, 595 (1948); herein incorporated by reference in its entirety). A mucoid isolate of BW30270 was included as a positive control.

Example X

This example describes Transmission Electron Microscopy (TEM) used in experiments conducted during the course of the present invention. Cultures of cells growing in early log phase in LB media at 37° C. were fixed in 2% osmium tetroxide for 90 minutes at room temperature. Cells were washed 3 times with distilled water before being incubated with 2% uranyl acetate contrast solution for 1 hour at room temperature. Cells were once again washed 3 times with distilled water, and then dehydrated by a series of increasing ethanol washes (30%, 50%, 70%, 90% and abs. ethanol for 15 min each at room temperature). Dehydrated cells were twice bathed in propylene oxide for 15 min each at room temperature, followed by impregnation in a propylene oxide/Epon mixture (1:1, v/v) by overnight incubation at 4° C. Polymerization was then performed overnight at 60° C. The block was sliced into ultra-thin sections (80-100 nm), placed on grids, and contrasted in a lead citrate solution. Images were acquired on a Philips CM-100 transmission electron microscope equipped with an automated compustage and Kodak 1.6 Megaplus high-resolution digital camera.

Example XI

This example describes Minimum Inhibitory Concentration (MIC) Determinations used in experiments conducted during the course of the present invention. The antibiotics used were from Sigma with the exception of cephaloridine, which was obtained from MicroSource Discovery Systems. Antibiotics were chosen based on their varying mode of action and entry into the cell. The MICs of all antibiotics and drugs studied were measured in LB media using the standard serial microdilution method as described (see, e.g., R. Vuorio, M. Vaara, Antimicrob. Agents Chemother. 36, 826 (1992); herein incorporated by reference in its entirety). Colonies from LB agar plate were scraped and suspended in media (~$10^4$ cells per mL) with varying concentrations of antibiotics. Cultures were incubated with shaking (~200 rpm) at 37° C. for 18 hours at which point growth was scored by visual inspection. The reported MIC values reported were interpreted as the lowest concentration of a drug that completely inhibited growth.

Example XII

This example describes a Human TNFα Cytokine Assay used in experiments conducted during the course of the present invention. The tumor necrosis factor (TNF) α cytokine-inducing capabilities of LPS preparations isolated as described above on human mononuclear cells (MNCs) were measured using an enzyme-linked immunoabsorbent assay (ELISA). LPS samples were resuspended in Hanks' Balanced Salt Solution by vigorous vortexing and aged overnight at 4° C. before being subjected to sonication/vortexing immediately prior to use. Heparinized blood drawn from healthy donors was directly mixed with an equal volume of Hanks' balanced salt solution and isolated by differential gradient centrifugation using the Leucosep system with Lymphoprep media from Greiner Bio-One according to the manufacturer's instructions. MNCs were washed twice with RPMI 1640 (3 mM L-glutamine, 100 units/mL penicillin, 100 μg/mL streptomycin) and were transferred to 96-well culture plates (7.5× $10^5$ cells/well). Stimulation of MNCs was performed as previously described (see, e.g., M. Mueller et al., J. Biol. Chem. 279, 26307 (2004); herein incorporated by reference in its entirety), and the supernatant was stored at 4° C. overnight. The hTNFα production was determined by an ELISA as described by Copeland, et al. (see, e.g., S. Copeland, H. S. Warren, S. F. Lowry, S. E. Calvano, D. Remick, Clin. Diagn. Lab. Immunol. 12, 60 (2005); herein incorporated by reference in its entirety). Data was collected in duplicate in three separate experiments with a representative data set reported in FIG. 7.

Example XIII

This Example describes the construction of the KPM22 Cosmid Library. A cosmid library was constructed from KPM22 genomic DNA by partial digestion with Sau3A, ligation into SuperCos1, and packaged using the Gigapack III XL packaging extract as described by the manufacturer (Stratagene). TCM15 was prepared for phage infection by growth in LB media containing 0.2% (w/v) maltose and 10 mM MgSO4 as well as additionally supplemented with A5P and G6P. Transformants were selected for growth on LB plates lacking supplemental sugar phosphates, along with the cosmid vector antibiotic resistance marker (100 μg mL-1 Amp). Cosmids were subcloned by partial Sau3A digestion followed by ligation into the BamHI site of the medium-copy number pMBL19 cloning vector (see, e.g., Nakano, Y., et al., Gene 162, 157-158 (1995); herein incorporated by reference in its entirety).

Example XIV

This example describes the materials used in experiments involving the gutQ gene. Primers were synthesized by Invitrogen. Genomic E. coli K-12 MG1655 DNA was purchased from American Type Culture Collection (ATCC 700926D). The Promega Wizard DNA purification kit was utilized for plasmid purification. Chemically competent E. coli XL1-Blue (Stratagene) and E. coli BL21(DE3) (Novagen) were used to host plasmid and protein expression, respectively. Strain BW30270 (rph$^+$, fnr$^+$), a derivative of E. coli K-12 MG1655, was obtained from the E. coli Genetic Stock Center (CGSC#7925). Sugar and sugar phosphates were purchased from Sigma-Aldrich, except for D-glucitol 6-phosphate which was prepared by the sodium tetraborohydride reduction of the D-glucose 6-phosphate (see, e.g., Bigham, E. C., et al., (1984) J Med Chem 27, 717-26; herein incorporated by reference in its entirety), purified by anion exchange chromatography (AG MP-1, Bio-Rad), and desalted by gel filtration (Bio-Gel P-2, Bio-Rad). Protein concentrations were determined using the Bio-Rad Protein Assay Reagent with BSA as the standard.

Example XV

This example describes the cloning, overexpression, and purification of the gutQ gene. The gutQ gene was amplified using standard PCR methodology with the F-R primer pair (Table 10), restricted with Nde I and BamH I, and directly ligated into similarly restricted linearized pT7-7 expression vector that had been treated with calf alkaline phosphatase.

TABLE 10

Nucleotide Sequences of Primers

| Primer | Sequence (5'-3') |
|---|---|
| F | (SEQ ID NO: 1)<br>GGTGCTAGAATT<u>CATATG</u>AGTGAAGCACTACTGAACG [a] |
| R | (SEQ ID NO: 2)<br>GAATTC<u>GGATCC</u>AAGTTAAATAATCCCGGCCTGATAGAAATCCTGC [b] |
| GQF | (SEQ ID NO: 3)<br>GATCGATGTGATCATAACCGGAGAGAGCAATGAGTGAAGCGTGTAGGCTGGAGCTGCTTC |
| GQR | (SEQ ID NO: 4)<br>CGGCTGGCGAAACGTCTGGGATTGAAGGATTAAATAATCCATTCCGGGGATCCGTCGACC |
| KDF | (SEQ ID NO: 5)<br>GCGATGTTGTACTGGTTATCGCCAATACTCGTTGAATAACTGGAAACGCATTGTGTAGGCTGGAGCTGCTTCG |
| KDR | (SEQ ID NO: 6)<br>GCGACGCACCTGCTTTGCTCATTGTTGTTTATCCTTGAATCTTTACACTACGGATATGAATATCCTCCTTAG |
| GDF | (SEQ ID NO: 7)<br>ATGAATCAGGTTGCCGTTGTC |
| GDR | (SEQ ID NO: 8)<br>CACCAGATTCACCTGTAGCG |

[a] Nde I site underlined.
[b] BamH I site underlined.

The ligation mixtures were used to transform chemically competent *E. coli* XL1-Blue cells, and transformants harboring the pT7-gutQ plasmid were identified by restriction analysis and DNA sequencing. *E. coli* BL21(DE3) cells were transformed with plasmid, rechecked by restriction analysis, and stored at –80° C. *E. coli* BL21(DE3)/pT7-gutQ cells were grown in 2×YT medium containing ampicillin (100 mg/L) at 37° C. with shaking (250 rpm). Once the culture reached the mid-logarithmic growth phase ($OD_{600}$~0.7-0.9), the culture was allowed to cool to 18° C. before being induced with isopropyl-β-D-thiogalactoside at a final concentration of 0.4 mM. After 16 hours of growth at 18° C., the cells were harvested by centrifugation (6,500×g, 15 min, 4° C.). The cell pellet was suspended in 20 mL of buffer A (20 mM Tris-HCl; 1 mM DL-dithiothreitol (DTT); pH=8.0) and then sonicated on ice (5×30 seconds; 2 minute pauses between pulses). Cellular debris was removed by centrifugation (29,000×g, 40 min, 4° C.) and the supernatant was filtered through a 0.22 μM Millex® filter. The solution was loaded onto a Hi Load™ (16/10) Q Sepharose fast flow column that had been pre-equilibrated with buffer A. Protein was eluted using a 0-900 mM gradient of NaCl in buffer A over 120 minutes. Fractions containing primarily recombinant protein (~33 kDa) as determined by SDS-PAGE were pooled. A saturated solution of ammonium sulfate was slowly added with stirring at room temperature until 15% saturation was reached. The solution was clarified by centrifugation (29,000×g, 30 min, 22° C.), and the supernatant was bought to 30% saturation. The protein pellet was collected by centrifugation (29,000×g, 30 min, 22° C.), resuspended in buffer A, and dialyzed against 2 L of buffer A overnight at 4° C. Preparations were greater than ~95% homogeneous as judged by SDS-PAGE with a yield of 180 mg gutQ/L of cell culture.

Example XVI

This example describes gel electrophoresis methods used in experiments conducted during the course of the present invention. SDS-PAGE was performed on protein samples (~5-10 μg) under reducing conditions on a 12% polyacrylamide gel and stained with 0.25% Coomassie brilliant blue R250 solutions. LPS samples were analyzed by tricine-SDS PAGE (stacking 4% T, 3% C; separating 16.5% T, 6% C) (see, e.g., Lesse, A. J., et al., (1990) J Immunol Methods 126, 109-17; herein incorporated by reference in its entirety), and visualized by silver staining (see, e.g., Hitchcock, P. J. & Brown, T. M. (1983) J Bacteriol 154, 269-77; herein incorporated by reference in its entirety).

Example XVII

This example describes enzyme assays used in experiments conducted during the course of the present invention. API activity was determined by the discontinuous cysteine-carbazole colorimetric assay (see, e.g., Dische, Z., Borenfreund, E. (1951) J Biol Chem 192, 583-587; herein incorporated by reference in its entirety) adapted to 96-well microplates as previously described (see, e.g., Meredith, T. C. & Woodard, R. W. (2003) J Biol Chem 278, 32771-7; herein incorporated by reference in its entirety). All plates contained internal Ru5P standards and appropriate A5P controls in triplicate. One unit of enzyme activity is defined as the conversion of 1 μmol of sugar phosphate per minute at 37° C.

A second more sensitive coupled assay was developed to determine API activity in crude cell extracts that utilized 3-deoxy-D-manno-octulosonate 8-phosphate synthase (kdsA) from *Arabidopsis thaliana*. This enzyme catalyzes the irreversible stereospecific condensation of A5P and PEP to form 3-deoxy-D-manno-octulosonate 8-phosphate (KDO8P) and inorganic phosphate. Reaction mixtures containing 5 μL of a purified kdsA solution (3 mg/mL; 10 U/mg), 10 mM Ru5P, 6 mM PEP, and 1 mM EDTA in 40 uL of 100 mM Tris-HCl (pH=8.25) was incubated for 3 minutes at 37° C. The reaction was initiated by the addition of 10 μL of cell extract. After 5 minutes, reactions were quenched by adding 50 μL of 10% (w/v) trichloroacetic acid. KDO8P produced was determined by the Aminoff periodate-thiobarbituric acid assay (see, e.g., Sheflyan, G. Y., et al., (1998) Journal of the American Chemical Society 120, 11027-11032; herein incorporated by reference in its entirety). Under these conditions, kdsA was not rate limiting in the formation of KDO8P.

D-Glucitol 6-phosphate dehydrogenase (gutD) activity was measured using a continuous spectrophotometric assay by monitoring the formation of NADH at 340 nm. Enzyme solutions (100 mM Tris-HCl, pH=8.7, 5 mM $NAD^+$) were preincubated at 25° C. for 2 minutes before the reactions were initiated by the addition of D-glucitol 6-phosphate at a final concentration of 20 mM.

Example XVIII

This example describes the characterization of gutQ. The characterization of gutQ was similarly performed according to methods reported for ksdD (see, e.g., Meredith, T. C. & Woodard, R. W. (2003) J Biol Chem 278, 32771-7; herein incorporated by reference in its entirety). Briefly, for substrate specificity enzyme samples were diluted in 100 mM Trizma-HCl buffer (pH=8.25) and assayed by initiating the reaction with substrate (15 nM gutQ, 10 mM sugar, 1 mM EDTA). After 10 minutes at 37° C., reactions containing the potential alternate substrates D-arabinose, D-ribose 5-phosphate, D-glucose 6-phosphate (G6P), D-glucose 1-phosphate, D-glucosamine 6-phosphate, or D-mannose 6-phosphate were quenched and the presence of ketose was determined. Product appearance for D/L-glyceraldehyde 3-phosphate, D-erythrose 4-phosphate, and D-fructose 6-phosphate was assayed by $^{31}P$ NMR. Kinetic constants were determined at 37° C. using the discontinuous microplate assay and were initiated by the addition of substrate. Concentrations typically ranged from $0.2K_m$ to $10K_m$. After 2 minutes, the reactions (50 mM Tris-HCl at pH=8.25, 5 nM gutQ, 1 mM EDTA) were quenched, at which point approximately less than 10% of substrate had been consumed. Initial rates ($v_0$) were determined in triplicate and fit to the standard Michaelis-Menten equation using non-linear least-squares regression to determine $K_m$ and $k_{cat}$ values for both the formation and disappearance of Ru5P. The equilibrium constant ($K_{eq}$) was determined using $^{31}P$ NMR as described for kdsD (see, e.g., Meredith, T. C. & Woodard, R. W. (2003) J Biol Chem 278, 32771-7; herein incorporated by reference in its entirety). The pH optimum of gutQ was determined by diluting the enzyme in BTP buffer solutions of varying pH values (pH=6.25 to 10, adjusted at 37° C.). Activity was measured as outlined above in triplicate with a reaction time of 3 minutes (100 mM BTP, 15 nM gutQ, 10 mM A5P, 1 mM EDTA). Enzyme samples of gutQ as isolated were diluted in 100 mM Trizma-HCl buffer (pH=8.25) and incubated with various divalent metals or EDTA for 30 minutes at 4° C. Remaining activity was then assayed at 37° C. under saturating substrate conditions in triplicate with a 3 minute reaction time (15 nM gutQ, 10 mM A5P, 10 μM metal or EDTA).

Example XIX

This example describes E. coli strain construction and growth conditions for experiments involving gutQ. E. coli strain BW30270 was used as the host for chromosomal gutQ and kdsD gene disruptions using the phage λ Red recombinase system according to the procedure of Datsenko and Wanner (see, e.g., Datsenko, K. A. & Wanner, B. L. (2000) Proc Natl Acad Sci USA 97, 6640-5; herein incorporated by reference in its entirety). Kanamycin and chloramphenicol were used at 50 μg/mL. Primer pairs GQF-GQR and KDF-KDR with either pKD13(kan) or pKD3(cat) as template, respectively, were used to construct BW30270(ΔgutQ::kan) and BW30270(ΔkdsD::cat) and are listed in Table 10. The resistance markers were then excised using the FLP recombinase system as described (see, e.g., Datsenko, K. A. & Wanner, B. L. (2000) Proc Natl Acad Sci USA 97, 6640-5; herein incorporated by reference in its entirety). BW30270 (ΔgutQ ΔkdsD) was similarly constructed from BW30270 (ΔkdsD) using the GQF-GQR PCR product insert except media and plates were supplemented at all times with G6P (10 μM) and A5P (15 μM) for subsequent manipulations performed after electrotransformation. All strains used were colony purified, tested for loss of all antibiotic resistances, and the relevant locus sequenced to confirm expected deletion site.

Cultures were grown in either M9 minimal media (26) or MOPS minimal media (see, e.g., Neidhardt, F. C., Bloch, P. L. & Smith, D. F. (1974) J Bacteriol 119, 736-47; herein incorporated by reference in its entirety) supplemented with thiamine (1 μg/mL) and the indicated carbon source(s) at 37° C. with shaking (250 rpm). BW30270(ΔgutQ ΔkdsD) cultures were additionally supplemented with G6P (10 μM) and A5P (5-50 μM). Ampicillin (100 μg/mL) was added to those strains carrying the pT7-7 ($Amp^R$) plasmid.

Example XX

This example describes the preparation of cellular extracts for enzymatic assays, LPS analysis, and RT-PCR. Overnight cultures were grown in minimal media with glycerol (0.2%) as the sole carbon source and the indicated supplements. Cultures were diluted (1:20 v/v) into fresh minimal media and shaken for two hours at 37° C. to allow the bacteria to return to exponential growth. Cultures of BW30270(ΔgutQ ΔkdsD) were preinduced during this period in order to upregulate the hexose phosphate transport system (uhp) by adding A5P (5 μM) and G6P (10 μM). Cells were pelleted by centrifugation to remove traces of G6P (6,500×g, 5 min, 22° C.), and then innoculated into fresh media. Where indicated, 10 mM D-glucitol was added to the cultures, and growth continued for an additional four to six hours to allow for upregulation of the gut operon at which point culture all cultures were in early to mid log growth. Cells were harvested by centrifugation (6,500×g, 5 min, 4° C.). Fractions to be assayed for API and gutD activity were twice washed with a chilled 1% NaCl solution, and then resuspended in buffer (20 mM Tris-HCl, 1 mM DTT, pH=8.0). Cells were disrupted by sonication, clarified by centrifugation (29,000×g, 20 min, 4° C.), and frozen. Samples for LPS analysis were washed twice with Dulbecco phosphate-buffered saline, the pellets resuspended in lysis buffer (200 mM Tris (pH=6.8), 2% SDS, 4% 2-mercaptoethanol, 10% glycerol). Equal numbers of cells based on $OD_{600\ nm}$ were processed according to the method of Hitchcock and Brown (see, e.g., Hitchcock, P. J. & Brown, T. M. (1983) J Bacteriol 154, 269-77; herein incorporated by reference in its entirety). Cell pellets to be analyzed for RNA were rapidly resuspended in Max Bacterial Enhancement reagent and extracted using TRIzol (Invitrogen) according to the manufacturer's protocol. RNA samples were further purified by digestion with RNase-free DNase and isolated using the RNeasy mini kit (Qiagen). The quality of the RNA was inspected by agarose electrophoresis and quantified by UV absorbance at 260 nm. Qualitative RT-PCR was performed using the Superscript II One-Step RT-PCR system (Invitrogen) as directed with 1 pg of purified total RNA as template and GDF-GDR primers (0.2 µM) to amplify the first 342 base pairs of the gutD gene.

Example XXI

This example describes the purification and characterization of gutQ. Purification to homogeneity was achieved in two steps using Q-Sepharose anion exchange chromatography followed by ammonium sulfate precipitation. The protein appeared as a single, sharp high molecular weight band by SDS-PAGE (~33 kDa) and the specific activity was 329 U/mg. The biochemical properties of gutQ were determined to be similar to those of kdsD. The kinetic parameters, pH optima, lack of cofactor requirement, and quaternary structure were all comparable. Monosaccharides that share common functionalities with A5P were tested as potential alternative substrates for gutQ. In the cysteine-carbazole colorimetric assay, 2-ketohexoses and 2-ketopentoses form purple-red chromophores which absorb light at 540 nm (see, e.g., Dische, Z., Borenfreund, E. (1951) J Biol Chem 192, 583-587; herein incorporated by reference in its entirety). The conversion of aldose to ketose can be observed by measuring the increase in the ratio of absorbance at $A^{540\ nm}$ of sample to control. None of the sugars tested were converted to their respective ketose forms. The short chain phosphorylated aldoses D/L-glyceraldehyde 3-phosphate and D-erythrose 4-phosphate as well as D-fructose 6-phosphate served as alternate substrates as determined by $^{31}$P-NMR. Within the limits of detection, gutQ was shown to be a specific phosphosugar aldol-ketol isomerase for A5P and Ru5P.

Example XXII

Figure 8:
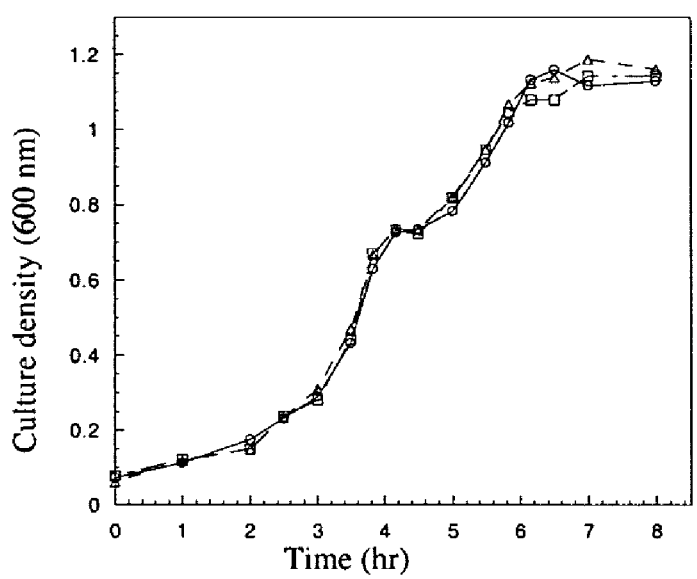
FIG. 8 shows the effect of gutQ on D-glucitol utilization and LPS biosynthesis. (A) Diauxic growth curves for BW30270 (□), BW30270(ΔgutQ) (○), and BW30270(pT7-gutQ) (Δ). Overnight cultures grown in M9 minimal media supplemented with 1 µg/mL thiamine and 10 mM D-glucose were diluted into fresh media with 2 mM D-glucose and 2 mM D-glucitol as dual carbon sources. Cell growth was monitored by measuring the turbidity at 600 nm. (B) Silver stained tricine SDS-PAGE LPS gels of proteinase K-treated whole cell lysates from BW30270 (WT), BW30270(ΔgutQ), and BW30270(ΔkdsD). Equal amounts of bacterial cells growing in minimal media (0.2% glycerol) with (+) or without (−) D-glucitol (10 mM) were harvested in early log phase and processed as described in Experimental procedures.
Figure 8:
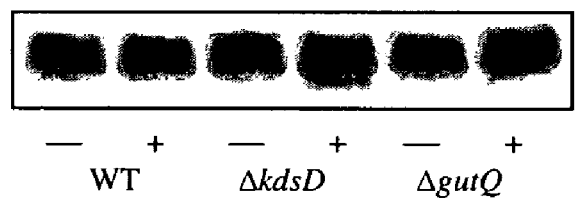

This example demonstrates that gutQ is capable of sustaining lipopolysaccharide biosynthesis. In order to assess the ability of gutQ to function as an API in vivo, BW30270 (ΔgutQ) and to BW30270(ΔkdsD) were constructed using the λ Red (γ, β, exo) homologous recombination system (see, e.g., Datsenko, K. A. & Wanner, B. L. (2000) Proc Natl Acad Sci USA 97, 6640-5; herein incorporated by reference in its entirety). Neither mutation was lethal, signaling the presence of other API encoding genes that can provide sufficient quantities of A5P needed for essential LPS biosynthesis. LPS gels indicated nearly equal amounts of the wild-type K-12 LPS core regardless of whether the gut operon was induced (see, FIG. 8A), suggesting A5P synthesis was not rate limiting in any of the strains under these growth conditions. Basal levels of gutQ in BW30270(ΔkdsD) were adequate to supply enough A5P to sustain viability and elaborate a functional LPS layer, strongly suggesting that gutQ functions as an API inside the cell.

Example XXIII

Figure 9:
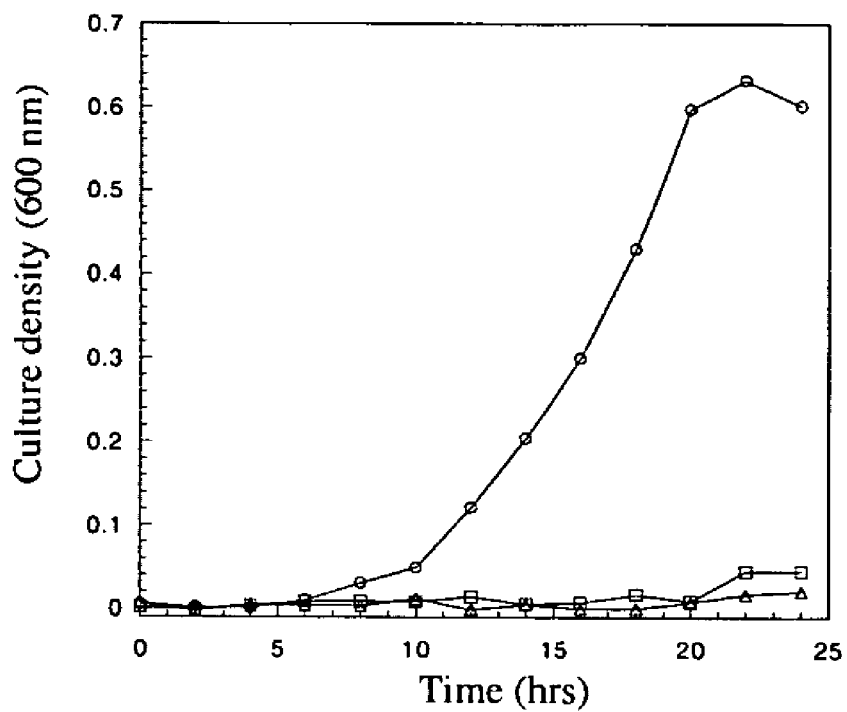
FIG. 9 shows growth and LPS synthesis in the ΔAPI strain BW30270(ΔgutQ ΔkdsD). (A) Growth curve of E. coli BW30270(ΔgutQ ΔyrbH) in MOPS minimal medium with thiamine (1 ug/mL) and glycerol (0.1%) as sole carbon source. Sugar phosphates were supplemented in the media with either 10 μM G6P (Δ), 15 μM A5P (□), or with both (○). (B) Titration of LPS with A5P. A stationary phase culture grown in MOPS minimal media (0.2% glycerol, 5 μM A5P, 10 μM G6P) that had ceased dividing was diluted into fresh media containing G6P (10 μM) and varying concentrations of A5P (0.1, 1, 10, 50, and 100 μM) and shaken for 6 hours. LPS samples were prepared from the same number of cells based on OD and analyzed by tricine SDS-PAGE and silver staining. (C) LPS tricine SDS-PAGE and (D) qualitative RT-PCR of gutD analysis of samples prepared from wildtype BW30270 (lanes 1 and 2) and BW30270(ΔgutQ ΔkdsD) (lanes 3 and 4). BW30270(ΔgutQ ΔkdsD) were preinduced with 10 μM G6P and 5 μM A5P, pelleted, resuspended in fresh MOPS minimal media (0.2% glycerol) with only A5P and 10 mM D-glucitol as indicated, and shaken for an additional 4 hours before harvesting for analyses. S—0.1-1 kb DNA molecular weight markers; Con—Genomic DNA as template.
Figure 9:
Figure 9:
Figure 9:

This example describes LPS biosynthesis in ΔAPI strain BW30270(ΔgutQ ΔkdsD). Both gutQ and kdsD genes in BW30270 were disrupted by utilizing the G6P inducible hexose phosphate transporter (uhp) to supply exogenous A5P. A5P is a high affinity, though non-inducible, substrate of the hexose phosphate transport system (uhp) (see, e.g., Kadner, R. J., Murphy, G. P. & Stephens, C. M. (1992) J Gen Microbiol 138 (Pt 10), 2007-14; Rick, P. D. & Osborn, M. J. (1972) Proc Natl Acad Sci USA 69, 3756-60; Eidels, L., Rick, P. D., Stimler, N. P. & Osborn, M. J. (1974) J Bacteriol 119, 138-43; each herein incorporated by reference in their entireties). MOPS-minimal media, which has a low concentration of inorganic phosphate (1.3 mM), was used to prevent inhibition of uhp mediated transport by inorganic phosphate (see, e.g., Shattuck-Eidens, D. M. & Kadner, R. J. (1981) J Bacteriol 148, 203-9; herein incorporated by reference in its entirety). The natural substrate of the uhp transporter G6P was required for efficient induction and transport of A5P into the cells. A5P or G6P alone was unable to restore growth as there was no detectable growth in the time course of study unless both A5P and G6P were included in the media (see, FIG. 9A). Thus, gutQ and kdsD were the sole intracellular sources of A5P for KDO synthesis. Cultures were supplemented with A5P in the media in order to enable lipopolysaccharide biosynthesis. By using overnight cultures from which A5P has been exhausted from the media as the innoculant and extended incubation times, the amount of mature LPS being synthesized in BW30270(ΔgutQ ΔkdsD) was dependent on the amount of A5P included in the media (FIG. 9B).

Example XXIV

This example describes expression of the gut operon. BW30270, BW30270(ΔgutQ), and BW30270(pT7-gutQ) were grown in M9 minimal media containing dual carbon sources, D-glucose and D-glucitol. All three strains grew at nearly identical rates, and exhibited the characteristic unusually long diauxic lag time of approximately 40 minutes after D-glucose had been exhausted from the media (see, e.g., Lengeler, J. & Lin, E. C. (1972) J Bacteriol 112, 840-8; herein incorporated by reference in its entirety). Under these conditions, induction was not influenced by gutQ. Strains BW30270, BW30270(ΔgutQ), and BW30270(ΔkdsD) were grown in M9 minimal media with glycerol as the carbon source. Glycerol is a class B carbon source and does not cause significant catabolite repression (see, e.g., Lengeler, J. W. (1986) Methods Enzymol 125, 473-85; herein incorporated by reference in its entirety), facilitating induction of the gut operon by D-glucitol through elevated cAMP levels. Total API (kdsD and/or gutQ) and gutD specific activities were measured in all three strains (Table 11).

TABLE 11

Specific activity of gutD and API in cell extracts

| E. coli Strains [a] | Glucitol [b] | gutD Activity [c] | API Activity [c,d] |
|---|---|---|---|
| WT | — | >1 | 14 ± 3 |
|  | + | 242 ± 14 | 48 ± 5 |
| ΔgutQ | — | >1 | 13 ± 3 |
|  | + | 374 ± 13 | 15 ± 2 |
| ΔkdsD | — | >1 | 2 ± 1 |
|  | + | 581 ± 48 | 46 ± 5 |
| pT7-gutQ | — | >1 | 2573 ± 78 |
|  | + | 323 ± 28 | 2457 ± 117 |

[a] Strains were grown in M9 minimal media with 0.2% glycerol as carbon source.
[b] D-glucitol was added at 10 mM to the cultures where indicated (+) 4 hours before harvesting.
[c] Specific activity reported in nmoles/min/mg.
[d] Values include kdsD and/or gutQ activity.

The gut operons of BW30270(ΔgutQ) and BW30270 (ΔkdsD) remained inducible, with only a 2-fold difference in degree of induction as estimated by gutD activity when compared to the parent BW30270 strain. Total API activity levels increased in both BW30270 and BW30270(ΔkdsD) when D-glucitol was added to the media, indicating gutQ is upregulated along with gutD. There was no change in observed API levels in BW30270(ΔgutQ) upon the addition of D-glucitol though the strain remains capable of upregulating gutD. A majority of API activity was attributable to kdsD in media lacking D-glucitol, confirming the identification of kdsD as the constitutively expressed LPS biosynthetic enzyme. BW30270(pT7-gutQ) was used to investigate the effect of elevated API levels on the gut operon (Table 10). Basal levels of API levels were increased ~250-fold in BW30270(pT7-gutQ) though no appreciable difference was observed in gutD levels as the operon remained repressed unless D-glucitol was provided in the media.

Example XXV

This example shows that A5P is important for upregulation of the gut operon. As no difference was observed in the regulation when a single API gene was disrupted, failure to directly observe the phenotype may have been due to suppression by the second copy of API. The inducibility of the gut operon was investigated in BW30270(ΔgutQ ΔkdsD). Overnight cultures were grown in MOPS minimal media (0.2% glycerol, 15 μM A5P, 10 μM G6P), and diluted into fresh media (0.2% glycerol, 5 μM A5P, 10 μM G6P) to return the cells to exponential growth. After 2 hours of shaking, the cells were harvested and used to innoculate media containing only glycerol and A5P. Since the cells were preinduced for the uhp transporter genes, no G6P was added. Two concentrations of A5P (5 and 50 μM) were chosen so that differences in the level of LPS and growth rates were minimal under the time course of study. At 50 μM A5P, gutD remained inducible to near wildtype levels (Table 12).

TABLE 12

Specific activity of gutD and gutQ$^{321}$ in ΔAPI cell extracts

| E. coli Strains[a] | glucitol[b] | A5P (μM) | gutD Activity[c] | gutQ Activity[c] |
|---|---|---|---|---|
| ΔgutQ ΔkdsD | — | 50 | >1 | N.D.[d] |
| | + | 50 | 278 ± 33 | N.D.[d] |
| | — | 5 | >1 | N.D.[d] |
| | + | 5 | 9.8 ± 1 | N.D.[d] |
| ΔgutQ ΔkdsD pT7-gutQ | — | 5 | >1 | 1366 ± 180 |
| | + | 5 | 356 ± 27 | 976 ± 101 |

[a] Strains were grown in MOPS minimal media with 0.2% glycerol and preinduced with 10 μM G6P/5 μM A5P
[b] D-glucitol was added at 10 mM to the cultures where indicated (+) 4 hours before harvesting.
[c] Specific activity reported in nmoles/min/mg.
[d] N.D. = no activity detected.

The gutQ protein product itself was not necessary for expression. When the A5P concentration was decreased to 5 μM, there was a marked and reproducible decrease in gutD activity in D-glucitol grown cells. The level of LPS, however, was only slightly reduced in comparison (FIG. 9C). This indicated a direct correlation between A5P levels and the amount of gutD, and that the difference was not due to the consequence of pleiotropic effects stemming from a depleted LPS layer. Analysis of the expression level of the gutD gene indicated the decrease in measured specific activity of gutD was correlated to the amount of mRNA (FIG. 9D). The gut operon remained inducible under the same growth conditions when complemented by a plasmid encoding gutQ.

Example XXVI

This example shows that the gene msbA, when overexpressed, allows ΔKDO E. coli bacterial cells to grow on agar without D-arabinose 5-phosphate media supplementation.

MsbA was originally identified as a multicopy suppressor of LpxL (HtrB) temperature-sensitive phenotypes (Polissi et al., 1996, Mol. Microbiol. 20:1221-1233, incorporated herein by reference in its entirety). Complementation of the auxotrophic TCM15 (E. coli) strain with a cosmid library of KPM22 genomic DNA revealed that msbA was a multicopy suppressor of the ΔKdo phenotype. Seventeen separate cosmid clones were isolated containing the msbA locus. A cosmid subclone (pMMW52), containing a 3.5 kb insert with only an intact wildtype msbA sequence identical to the wild-type, was able to directly rescue TCM15, as judged by loss of A5P auxotrophy and restoration of colony-forming ability on solid agar. The growth rate of TCM15 (pMMW52) is strikingly similar to KPM22 E. coli strain (Meredith et al., 2006, ACS Chem. Biol. 1:33-42, incorporated herein by reference in its entirety).

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. An isolated viable Gram-negative bacterial strain, wherein said strain comprises a first mutation leading to a disruption of the $KDO_2$-Lipid$IV_A$ biosynthetic pathway, and a second mutation in a gene selected from msbA or yjhD, and wherein said bacterial strain lacks KDO and displays Lipid$IV_A$ in its outer membrane.

2. The bacterial strain of claim 1, wherein said first mutation resides in a gene selected from the group consisting of gutQ, kdsD, kdsA, kdsB, and waaA.

3. The bacterial strain of claim 1, wherein said first mutation results in a lack of expression of D-arabinose 5-phosphate isomerase (API).

4. The bacterial strain of claim 1, said second mutation is in the msbA gene.

5. The bacterial strain of claim 1, said strain comprising a mutation in the yjhD gene.

6. The bacterial strain of claim 1, further comprising at least one mutation in the lpxL or lpxM gene.

7. The bacterial strain of claim 1, wherein said strain is selected from the group consisting of *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., *Corynebacteria* spp., *Citrobacter* spp., *Chlamydia* spp., *Brucella* spp., *Pseudomonas* spp., *Helicobacter* spp, and *Vibrio* spp.

8. The bacterial strain of claim 1, wherein said strain is selected from the group consisting of *Escherichia* spp., *Salmonella* spp., and *Pseudomonas* spp.

9. The bacterial strain of claim 1, wherein said strain is *E. coli*.

10. The bacterial strain of claim 1, wherein said strain is transformed with a gene of interest operably linked to a promoter.

11. The bacterial strain of claim 10, wherein said gene of interest is on a plasmid and is expressed in said bacterial strain.

12. A composition comprising an outer membrane of the viable *Escherichia coli* strain of claim 10.

13. A composition, comprising the viable *Escherichia coli* strain of claim 10.

14. A composition comprising the viable Gram-negative bacterial strain of claim 1.

15. The composition of claim 14, wherein said viable Gram-negative bacterial strain lacks D-arabinose 5-phosphate isomerase (API) expression.

16. A method of producing Lipid $IV_A$, comprising extracting Lipid $IV_A$ from said viable Gram-negative bacterial strain of claim 1.

* * * * *

UNITED STATES PATENT AND TRADEMARK OFFICE
CERTIFICATE OF CORRECTION

| | | |
|---|---|---|
| PATENT NO. | : 8,303,964 B2 | Page 1 of 1 |
| APPLICATION NO. | : 11/655413 | |
| DATED | : November 6, 2012 | |
| INVENTOR(S) | : Woodard et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1388 days.

Signed and Sealed this
Ninth Day of June, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: Synthetic

<400> SEQUENCE: 1
ggtgctagaa ttcatatgag tgaagcacta ctgaacg          37

<210> SEQ ID NO 2
<211> LENGTH: 46
<212> TYPE: DNA
<213> ORGANISM: Artificial Sequence
<220> FEATURE:

<223> OTHER INFORMATION: Synthetic

<400> SEQUENCE: 2
gaattcggat ccaagttaaa taatcccggc ctgatagaaa tcctgc      46

<210> SEQ ID NO 3
<211> LENGTH: 60
<212> TYPE: DNA
<213> ORGANISM: Artificial Sequence
<220> FEATURE:
<223> OTHER INFORMATION: Synthetic

<400> SEQUENCE: 3
gatcgatgtg atcataaccg gagagagcaa tgagtgaagc gtgtaggctg gagctgcttc      60

<210> SEQ ID NO 4
<211> LENGTH: 60
<212> TYPE: DNA
<213> ORGANISM: Artificial Sequence
<220> FEATURE:
<223> OTHER INFORMATION: Synthetic

<400> SEQUENCE: 4
cggctggcga aacgtctggg attgaaggat taaataatcc attccgggga tccgtcgacc      60

<210> SEQ ID NO 5
<211> LENGTH: 73
<212> TYPE: DNA
<213> ORGANISM: Artificial Sequence
<220> FEATURE:
<223> OTHER INFORMATION: Synthetic

<400> SEQUENCE: 5
gcgatgttgt actggttatc gccaatactc gttgataaac tggaaacgca ttgtgtaggc      60
tggagctgct tcg      73

<210> SEQ ID NO 6
<211> LENGTH: 72
<212> TYPE: DNA
<213> ORGANISM: Artificial Sequence
<220> FEATURE:
<223> OTHER INFORMATION: Synthetic

<400> SEQUENCE: 6
gcgacgcacc tgctttgctc attgttgttt atccttgaat ctttacacta cggatatgaa      60
tatcctcctt ag      72

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
atgaatcagg ttgccgttgt c      21

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8

```
caccagattc acctgtagcg                                                 20

<210> SEQ ID NO 9
<211> LENGTH: 65
<212> TYPE: DNA
<213> ORGANISM: Artificial Sequence
<220> FEATURE:
<223> OTHER INFORMATION: Synthetic

<400> SEQUENCE: 9
gctgcattaa ttaatcgaca ttttactcaa gattaaggcg atcctgtgta ggctggagct    60
gcttc                                                                65

<210> SEQ ID NO 10
<211> LENGTH: 65
<212> TYPE: DNA
<213> ORGANISM: Artificial Sequence
<220> FEATURE:
<223> OTHER INFORMATION: Synthetic

<400> SEQUENCE: 10
gtcttaacgc agaacgctaa tactttattt ttcaagcaaa aaagaattcc ggggatccgt    60
cgacc                                                                65

<210> SEQ ID NO 11
<211> LENGTH: 70
<212> TYPE: DNA
<213> ORGANISM: Artificial Sequence
<220> FEATURE:
<223> OTHER INFORMATION: Synthetic

<400> SEQUENCE: 11
acagctaaat acatagaatc cccagcacat ccataagtca gctatttact gtgtaggctg    60
gagctgcttc                                                           70

<210> SEQ ID NO 12
<211> LENGTH: 70
<212> TYPE: DNA
<213> ORGANISM: Artificial Sequence
<220> FEATURE:
<223> OTHER INFORMATION: Synthetic

<400> SEQUENCE: 12
taatgggatc gaaagtaccc ggataaatcg cccgttttttg cataacaacc catatgaata   60
tcctccttag                                                           70
```